US012571802B2

(12) United States Patent
MacDonald et al.

(10) Patent No.: US 12,571,802 B2
(45) Date of Patent: Mar. 10, 2026

(54) NANOSWITCH CALIPER TRAINS FOR HIGH-THROUGHPUT, HIGH-RESOLUTION STRUCTURAL ANALYSIS OF BIOMOLECULES

(71) Applicants: President and Fellows of Harvard College, Cambridge, MA (US); Children's Medical Center Corporation, Boston, MA (US); Dana-Farber Cancer Institute, Inc., Boston, MA (US)

(72) Inventors: James I. MacDonald, Cambridge, MA (US); Michael H. Raez, Cambridge, MA (US); William M. Shih, Cambridge, MA (US); Wesley Philip Wong, Cambridge, MA (US)

(73) Assignees: President and Fellows of Harvard College, Cambridge, MA (US); Children's Medical Center Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 723 days.

(21) Appl. No.: 17/907,763

(22) PCT Filed: Feb. 26, 2021

(86) PCT No.: PCT/US2021/020010
§ 371 (c)(1),
(2) Date: Aug. 29, 2022

(87) PCT Pub. No.: WO2021/174071
PCT Pub. Date: Sep. 2, 2021

(65) Prior Publication Data
US 2023/0146476 A1 May 11, 2023

Related U.S. Application Data

(60) Provisional application No. 62/983,648, filed on Feb. 29, 2020.

(51) Int. Cl.
*G01N 33/68* (2006.01)
*C12Q 1/6811* (2018.01)
(Continued)

(52) U.S. Cl.
CPC ....... *G01N 33/6803* (2013.01); *C12Q 1/6811* (2013.01); *G01N 33/5308* (2013.01); *G01N 33/54346* (2013.01)

(58) Field of Classification Search
CPC ................ C12Q 1/6811; C12Q 1/6816; C12Q 2565/631; G01N 33/5308; G01N 33/54346; G01N 33/6803
See application file for complete search history.

(56) References Cited

U.S. PATENT DOCUMENTS

| | | | |
|---|---|---|---|
| 5,571,677 A | 11/1996 | Gryaznov | |
| 5,635,352 A | 6/1997 | Urdea et al. | |

(Continued)

FOREIGN PATENT DOCUMENTS

| | | |
|---|---|---|
| JP | H06-508753 A | 10/1994 |
| JP | 2000-312589 A | 8/2000 |

(Continued)

OTHER PUBLICATIONS

Invitation to Pay Additional Fees mailed May 11, 2021, for PCT/US2021/020010.

(Continued)

*Primary Examiner* — Jennifer Wecker
(74) *Attorney, Agent, or Firm* — Wolf, Greenfield & Sacks, P.C.

(57) ABSTRACT

Provided herein are compositions and methods for determining the structure of individual targets by determining long-range distances within such targets.

20 Claims, 9 Drawing Sheets

Specification includes a Sequence Listing.

(51) Int. Cl.
*G01N 33/53* (2006.01)
*G01N 33/543* (2006.01)

(56) References Cited

U.S. PATENT DOCUMENTS

| | | | |
|---|---|---|---|
| 5,888,731 | A | 3/1999 | Yager et al. |
| 5,902,724 | A | 5/1999 | Lane et al. |
| 6,143,504 | A | 11/2000 | Das et al. |
| 6,232,066 | B1 | 5/2001 | Felder et al. |
| 6,251,660 | B1 | 6/2001 | Muir et al. |
| 6,569,306 | B1 | 5/2003 | Read et al. |
| 6,770,698 | B1 | 8/2004 | Chu et al. |
| 8,129,119 | B2 | 3/2012 | Jarrell et al. |
| 8,491,454 | B2 | 7/2013 | Wong et al. |
| 8,795,143 | B2 | 8/2014 | Wong et al. |
| 9,255,905 | B1 | 2/2016 | Mellors et al. |
| 9,914,958 | B2 | 3/2018 | Wong et al. |
| 9,994,839 | B2 | 6/2018 | Lo et al. |
| 10,919,037 | B2 | 2/2021 | Wong et al. |
| 11,198,900 | B2 | 12/2021 | Koussa et al. |
| 11,396,650 | B2 | 7/2022 | Wong et al. |
| 11,591,636 | B2 | 2/2023 | Wong et al. |
| 11,713,483 | B2 | 8/2023 | Wong et al. |
| 12,077,807 | B2 | 9/2024 | Chandrasekaran et al. |
| 12,123,869 | B2 | 10/2024 | Hansen et al. |
| 12,331,349 | B2 | 6/2025 | Wong et al. |
| 2002/0081744 | A1 | 6/2002 | Chan et al. |
| 2002/0182717 | A1 | 12/2002 | Karlsson et al. |
| 2003/0143549 | A1 | 7/2003 | Yang et al. |
| 2003/0186301 | A1 | 10/2003 | Christian et al. |
| 2006/0194240 | A1 | 8/2006 | Arnold, Jr. et al. |
| 2006/0257958 | A1 | 11/2006 | Bruno |
| 2007/0026423 | A1 | 2/2007 | Koehler et al. |
| 2007/0037152 | A1 | 2/2007 | Drmanac |
| 2007/0117109 | A1 | 5/2007 | Rothemund |
| 2007/0154899 | A1 | 7/2007 | Coull et al. |
| 2007/0184054 | A1* | 8/2007 | Greif ..................... A61P 43/00 |
| | | | 536/23.53 |
| 2007/0281367 | A1 | 12/2007 | Hennessy et al. |
| 2008/0038725 | A1 | 2/2008 | Luo et al. |
| 2008/0044834 | A1 | 2/2008 | Heyduk |
| 2008/0131870 | A1 | 6/2008 | Allawi et al. |
| 2008/0312103 | A1 | 12/2008 | Nemoto et al. |
| 2009/0087838 | A1 | 4/2009 | Reif et al. |
| 2009/0118140 | A1 | 5/2009 | Suzara |
| 2009/0286694 | A1 | 11/2009 | Zainiev et al. |
| 2010/0015608 | A1 | 1/2010 | Kolpashchikov |
| 2010/0035247 | A1 | 2/2010 | Burton |
| 2010/0206730 | A1 | 8/2010 | Hunkapiller et al. |
| 2010/0216658 | A1 | 8/2010 | Chaput et al. |
| 2011/0086774 | A1 | 4/2011 | Dunaway |
| 2011/0268654 | A1 | 11/2011 | Hilderbrand et al. |
| 2013/0004523 | A1 | 1/2013 | Zubarev et al. |
| 2013/0130884 | A1 | 5/2013 | Wong et al. |
| 2013/0196341 | A1 | 8/2013 | Neely et al. |
| 2013/0310260 | A1 | 11/2013 | Kim et al. |
| 2013/0344508 | A1 | 12/2013 | Schwartz et al. |
| 2014/0255939 | A1 | 9/2014 | Wong et al. |
| 2014/0284213 | A1 | 9/2014 | Sabin et al. |
| 2014/0302532 | A1 | 10/2014 | Wilson et al. |
| 2015/0027894 | A1 | 1/2015 | Puleo et al. |
| 2015/0093836 | A1 | 4/2015 | Suzuki et al. |
| 2015/0099650 | A1 | 4/2015 | Sood et al. |
| 2015/0292007 | A1 | 10/2015 | Church et al. |
| 2015/0361422 | A1 | 12/2015 | Sampson et al. |
| 2016/0186238 | A1 | 6/2016 | Liu et al. |
| 2017/0369935 | A1 | 12/2017 | Koussa et al. |
| 2018/0135043 | A1 | 5/2018 | Wong et al. |
| 2018/0223344 | A1 | 8/2018 | Chandrasekaran et al. |
| 2018/0274001 | A1* | 9/2018 | Efcavitch ....... C12Y 207/07007 |
| 2018/0291434 | A1 | 10/2018 | Wong et al. |
| 2019/0048409 | A1 | 2/2019 | Wong et al. |
| 2019/0070604 | A1 | 3/2019 | Wong et al. |
| 2020/0116712 | A1 | 4/2020 | Hansen et al. |
| 2020/0340033 | A1 | 10/2020 | Wong et al. |
| 2021/0355483 | A1* | 11/2021 | Chee ..................... G01N 33/68 |
| 2023/0045556 | A1 | 2/2023 | Wong et al. |
| 2024/0018577 | A1 | 1/2024 | Wong et al. |
| 2024/0076715 | A1 | 3/2024 | Wong et al. |
| 2025/0003957 | A1 | 1/2025 | Hansen et al. |
| 2025/0034619 | A1 | 1/2025 | Chandrasekaran et al. |

FOREIGN PATENT DOCUMENTS

| | | |
|---|---|---|
| JP | 2003-219897 A | 8/2003 |
| JP | 2005-536234 A | 12/2005 |
| JP | 2008-259453 A | 10/2008 |
| JP | 2009-521230 | 6/2009 |
| WO | WO 1993/01313 A1 | 1/1993 |
| WO | WO 1998/18961 A1 | 5/1998 |
| WO | WO 00/40751 A2 | 7/2000 |
| WO | WO 2004/016767 A2 | 2/2004 |
| WO | WO 2007/076128 A2 | 7/2007 |
| WO | WO 2009/045906 A2 | 4/2009 |
| WO | WO 2011/005221 A1 | 1/2011 |
| WO | WO 2011/153211 A1 | 12/2011 |
| WO | WO 2012/057689 A1 | 5/2012 |
| WO | WO 2012/058638 A2 | 5/2012 |
| WO | WO 2013/010023 A2 | 1/2013 |
| WO | WO 2013/067489 A1 | 5/2013 |
| WO | WO 2014/011800 A1 | 1/2014 |
| WO | WO 2014/160192 A1 | 10/2014 |
| WO | WO 2015/006626 A1 | 1/2015 |
| WO | WO 2015/040009 A1 | 3/2015 |
| WO | WO 2015/164602 A2 | 10/2015 |
| WO | WO 2016/089588 A1 | 6/2016 |
| WO | WO 2016/164866 A1 | 10/2016 |
| WO | WO 2016/196824 A1 | 12/2016 |
| WO | WO 2017/003950 A2 | 1/2017 |
| WO | WO 2017/139409 A1 | 8/2017 |
| WO | WO 2017/147398 A1 | 8/2017 |
| WO | WO 2017/165647 A1 | 9/2017 |
| WO | WO 2018/106721 A1 | 6/2018 |
| WO | WO 2019/100080 A1 | 5/2019 |

OTHER PUBLICATIONS

International Search Report and Written Opinion mailed Jul. 23, 2021, for PCT/US2021/020010.

International Preliminary Report on Patentability mailed Sep. 15, 2022, for PCT/US2021/020010.

[No Author Listed], Wikipedia Entry, "Xhol." May 14, 2014. Retrieved from the internet. <https://en.wikipedia.org/w/index/php?title=Xhol&oldid=608536958>. Retrieved on Oct. 18, 2016.

Aaij et al., The gel electrophoresis of DNA. Biochim Biophys Acta. May 10, 1972;269(2):192-200.

Ando et al., Single-nanoparticle tracking with angstrom localization precision and microsecond time resolution. Biophys J. Dec. 18, 2018;115(12):2413-2427. Epub Nov. 17, 2018.

Baslé et al., Protein chemical modification on endogenous amino acids. Chem Biol. Mar. 26, 2010;17(3):213-27.

Bellot et al., Recovery of intact DNA nanostructures after agarose gel-based separation. Nat Methods. Mar. 2011;8(3):192-4. doi: 10.1038/nmeth0311-192.

Bishop et al., Electrophoretic separation of viral nucleic acids on polyacrylamide gels. J Mol Biol. Jun. 28, 1967;26(3):373-87.

Bustamante et al., Entropic elasticity of lambda-phage DNA. Science. Sep. 9, 1994;265(5178):1599-600.

Bustamante et al., Ten years of tension: single-molecule DNA mechanics. Nature. Jan. 23, 2003;421(6921):423-7.

Butko et al., Detection of Ligand-Induced Conformational Changes in Oligonucleotides by Second-Harmonic Generation at a Supported Lipid Bilayer Interface. Anal Chem. Nov. 1, 2016;88(21):10482-10489. Epub Oct. 12, 2016. Accepted Manuscript, 23 pages.

Chandrasekaran et al., Label-free Detection of Specific Nucleic Acid Sequences using DNA Nanoswitches. The RNA Institute , University at Albany, State University of New York.

Chandrasekaran et al., Programmable DNA Nanoswitches for Detection of Nucleic Acid Sequences. ACS Sens., 2016, 1 (2), pp. 120-123.

(56)　　　　　References Cited

OTHER PUBLICATIONS

Cheezum et al., Quantitative comparison of algorithms for tracking single fluorescent particles. Biophys J. Oct. 2001;81(4):2378-88.

Cheng et al., Early pregnancy factor in cervical mucus of pregnant women. Am J Reprod Immunol. Feb. 2004;51(2):102-5.

Chilkoti et al., Molecular Origins of the Slow Streptavidin-Biotin Dissociation Kinetics. J Am Chem Soc. 1995;117(43):10622-8.

Chivers et al., A streptavidin variant with slower biotin dissociation and increased mechanostability. Nat Methods. May 2010;7(5):391-3. doi: 10.1038/nmeth.1450. Epub Apr. 11, 2010.

Cho et al., A genomic-scale view of the cAMP response element-enhancer decoy: a tumor target-based genetic tool. Proc Natl Acad Sci U S A. Nov. 26, 2002;99(24):15626-31. Epub Nov. 18, 2002.

Conde et al., Implantable hydrogel embedded dark-gold nanoswitch as a theranostic probe to sense and overcome cancer multidrug resistance. Proc Natl Acad Sci U S A. Mar. 17, 2015;112(11):E1278-87. doi: 10.1073/pnas.1421229112. Epub Mar. 2, 2015.

Deniz et al., Single-molecule biophysics: at the interface of biology, physics and chemistry. J R Soc Interface. Jan. 6, 2008;5(18):15-45.

Devaraj et al., Biomedical applications of tetrazine cycloadditions. Acc Chem Res. Sep. 20, 2011;44(9):816-27. doi: 10.1021/ar200037t. Epub May 31, 2011.

Doshi et al., In vitro nanobody discovery for integral membrane protein targets. Sci Rep. Oct. 24, 2014;4:6760. doi: 10.1038/srep06760.

Douglas et al., A logic-gated nanorobot for targeted transport of molecular payloads. Science. Feb. 17, 2012;335(6070):831-4. doi: 10.1126/science.1214081.

Douglas et al., Self-assembly of DNA into nanoscale three-dimensional shapes. Nature. May 21, 2009;459(7245):414-8. doi: 10.1038/nature08016.

Evans et al., Dynamic strength of molecular adhesion bonds. Biophys J. Apr. 1997;72(4):1541-55.

Evans et al., Forces and bond dynamics in cell adhesion. Science. May 25, 2007;316(5828):1148-53.

Evans, Probing the relation between force—lifetime—and chemistry in single molecular bonds. Annu Rev Biophys Biomol Struct. 2001;30:105-28.

Fang et al., Tuning surface states to achieve the modulated fluorescence of carbon dots for probing the activity of alkaline phosphatase and immunoassay of alpha-fetoprotein. Sensors and Actuators B: Chemical. 2018;257:620-628.

França et al., A review of DNA sequencing techniques. Q Rev Biophys. May 2002;35(2):169-200.

Fu et al., Flow-induced elongation of von Willebrand factor precedes tension-dependent activation. Nat Commun. Aug. 23, 2017;8(1):324.

Green, Avidin and streptavidin. Methods Enzymol. 1990;184:51-67.

Greenleaf et al., High-resolution, single-molecule measurements of biomolecular motion. Annu Rev Biophys Biomol Struct. 2007;36:171-90.

Halvorsen et al., Binary DNA nanostructures for data encryption. PLoS One. 2012;7(9):e44212. doi: 10.1371/journal.pone.0044212. Epub Sep. 11, 2012.

Halvorsen et al., Cross-platform comparison of nucleic acid hybridization: toward quantitative reference standards. Anal Biochem. Nov. 15, 2014;465:127-33. doi: 10.1016/j.ab.2014.08.001. Epub Aug. 12, 2014.

Halvorsen et al., Massively parallel single-molecule manipulation using centrifugal force. Biophys J. Jun. 2, 2010;98(11):L53-5.

Halvorsen et al., Nanoengineering a single-molecule mechanical switch using DNA self- assembly. Nanotechnology. Dec. 9, 2011;22(49):494005. doi: 10.1088/0957-4484/22/49/494005. Epub Nov. 21, 2011.

Halvorsen, Probing Weak Single-Molecule Interactions: Development and Demonstration of a New Instrument. Boston University, College of Engineering dissertation. 2007: 102 pages.

Hanke et al., Entropy loss in long-distance DNA looping. Biophys J. Jul. 2003;85(1):167-73.

Hansen et al., Nanoswitch-linked immunosorbent assay (NLISA) for fast, sensitive, and specific protein detection. PNAS. Sep. 26, 2017;114(39):10367-10372. Supporting Information, 4 pages.

Hassur et al., UV shadowing—a new and convenient method for the location of ultraviolet-absorbing species in polyacrylamide gels. Anal Biochem. May 1974;59(1):162-4.

Hellman et al., Electrophoretic mobility shift assay (EMSA) for detecting protein-nucleic acid interactions. Nat Protoc. 2007;2(8):1849-61.

Hopwood et al., Integrated microfluidic system for rapid forensic DNA analysis: sample collection to DNA profile. Anal Chem. Aug. 15, 2010;82(16):6991-9. doi: 10.1021/ac101355r.

Horn et al., Forks and combs and DNA: the synthesis of branched oligodeoxyribonucleotides. Nucleic Acids Res. Sep. 12, 1989;17(17):6959-67.

Idili et al., Programmable pH-triggered DNA nanoswitches. J Am Chem Soc. Apr. 23, 2014;136(16):5836-9. doi: 10.1021/ja500619w. Epub Apr. 9, 2014. Abstract only.

Jiang et al., Electrostatic steering enables flow-activated von willebrand factor to bind platelet glycoprotein, revealed by single-molecule stretching and imaging. J Mol Biol. Mar. 29, 2019;431(7):1380-1396. Epub Feb. 22, 2019.

Jiang et al., Stretching DNA to twice the normal length with single-molecule hydrodynamic trapping. Lab Chip. May 19, 2020;20(10):1780-1791.

Jones et al., Nanomaterials. Programmable materials and the nature of the DNA bond. Science. Feb. 20, 2015;347(6224):1260901. doi: 10.1126/science.1260901.

Jung et al., Binding and Dissociation Kinetics of Wild-Type and Mutant Streptavidins on Mixed Biotin-Containing Alkylthiolate Monolayers. Langmuir. Nov. 28, 2000;16(24): 9421-32.

Khalil et al., Single M13 bacteriophage tethering and stretching. Proc Natl Acad Sci U S A. Mar. 20, 2007;104(12):4892-7. Epub Mar. 13, 2007.

Kim et al., A mechanically stabilized receptor-ligand flex-bond important in the vasculature. Nature. Aug. 19, 2010;466(7309):992-5. doi: 10.1038/nature09295.

Kleiner et al., Small-molecule discovery from DNA-encoded chemical libraries. Chem Soc Rev. Dec. 2011;40(12):5707-17. doi: 10.1039/c1cs15076f. Epub Jun. 14, 2011.

Klumb et al., Energetic roles of hydrogen bonds at the ureido oxygen binding pocket in the streptavidin-biotin complex. Biochemistry. May 26, 1998;37(21):7657-63.

Koch et al., Prospects and limitations of the rosette inhibition test to detect activity of early pregnancy factor in the pig. J Reprod Fertil. May 1985;74(1):29-38.

Koussa et al., DNA nanoswitches: a quantitative platform for gel-based biomolecular interaction analysis. Nat Methods. Feb. 2015;12(2):123-6. doi: 10.1038/nmeth.3209. Epub Dec. 8, 2014.

Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.

Kufer et al., Single-molecule cut-and-paste surface assembly. Science. Feb. 1, 2008;319(5863):594-6. doi:10.1126/science.1151424.

Leier et al., Cryptography with DNA binary strands. Biosystems. Jun. 2000;57(1):13-22.

Lubken et al., Multiplexed Continuous Biosensing by Single-Molecule Encoded Nanoswitches. Nano Lett. Apr. 8, 2020;20(4):2296-2302. doi: 10.1021/acs.nanolett.9b04561. Epub Mar. 12, 2020.

Mcdonell et al., Analysis of restriction fragments of T7 DNA and determination of molecular weights by electrophoresis in neutral and alkaline gels. J Mol Biol. Feb. 15, 1977;110(1):119-46.

Mendoza et al., Probing protein structure by amino acid-specific covalent labeling and mass spectrometry. Mass Spectrom Rev. Sep.-Oct. 2009;8(5):785-815.

Modi et al., A DNA nanomachine that maps spatial and temporal pH changes inside living cells. Nat Nanotechnol. May 2009;4(5):325-30. doi: 10.1038/nnano.2009.83. Epub Apr. 6, 2009. Abstract only.

Morton et al., Early pregnancy factor. Semin Reprod Endocrinol. May 1992;10:72-82.

(56) References Cited

OTHER PUBLICATIONS

Morton et al., Rosette inhibition test: A multicentre investigation of early pregnancy factor in humans. J Reprod Immunol. Sep. 1982;4(5):251-61.

Neuman et al., Single-molecule force spectroscopy: optical tweezers, magnetic tweezers and atomic force microscopy. Nat Methods. Jun. 2008;5(6):491-505. doi: 10.1038/nmeth.1218.

Papadakis et al., Acoustic characterization of nanoswitch structures: application to the DNA Holliday Junction. Nano Lett. Dec. 8, 2010;10(12):5093-7. doi: 10.1021/nl103491v. Epub Nov. 1, 2010.

Park et al., Dual blockade of cyclic AMP response element- (CRE) and AP-1-directed transcription by CRE-transcription factor decoy oligonucleotide. gene-specific inhibition of tumor growth. J Biol Chem. Jan. 15, 1999;274(3):1573-80.

Pei et al., A DNA nanostructure-based biomolecular probe carrier platform for electrochemical biosensing. Adv Mater. Nov. 9, 2010;22(42):4754-8. doi: 10.1002/adma.201002767.

Ping, High Performing assay using antibody-conjugated DNA nanoswitches detects proteins. MRS Bulletin. 2017;42:780. 1 page.

Pinheiro et al., Challenges and opportunities for structural DNA nanotechnology. Nat Nanotechnol. Nov. 6, 2011;6(12):763-72.

Porchetta et al., Programmable Nucleic Acid Nanoswitches for the Rapid, Single-Step Detection of Antibodies in Bodily Fluids. J Am Chem Soc. Jan. 24, 2018;140(3):947-953. doi: 10.1021/jacs.7b09347. Epub Jan. 9, 2018.

Quek et al., Mechanically controlled binary conductance switching of a single-molecule junction. Nat Nanotechnol. Apr. 2009;4(4):230-4. doi:10.1038/nnano.2009.10. Epub Mar. 1, 2009.

Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.

Rothemund, Folding DNA to create nanoscale shapes and patterns. Nature. Mar. 16, 2006;440(7082):297-302.

Sacca et al., DNA origami: the art of folding DNA. Angew Chem Int Ed Engl. Jan. 2, 2012;51(1):58-66. doi: 10.1002/anie.201105846. Epub Dec. 7, 2011.

Seeman, DNA in a material world. Nature. Jan. 23, 2003;421(6921):427-31.

Seeman, Nanomaterials based on DNA. Annu Rev Biochem. 2010;79:65-87. doi: 10.1146/annurev-biochem-060308-102244.

Shroff et al., Biocompatible force sensor with optical readout and dimensions of 6 nm3. Nano Lett. Jul. 2005;5(7):1509-14.

Shroff et al., Optical measurement of mechanical forces inside short DNA loops. Biophys J. Mar. 15, 2008;94(6):2179-86. Epub Dec. 7, 2007.

Silver et al., Tethered-bead, immune sandwich assay. Biosens Bioelectron. Jan. 15, 2015;63:117-123. Epub Jul. 11, 2014.

Smith et al., Overstretching B-DNA: the elastic response of individual double-stranded and single-stranded DNA molecules. Science. Feb. 9, 1996;271(5250):795-9.

Strunz et al., Dynamic force spectroscopy of single DNA molecules. Proc Natl Acad Sci U S A. Sep. 28, 1999;96(20):11277-82.

Su et al., Nucleic acid fluorescent probes for biological sensing. Appl Spectrosc. Nov. 2012;66(11):1249-62. doi: 10.1366/12-06803. Review.

Svoboda et al., Direct observation of kinesin stepping by optical trapping interferometry. Nature. Oct. 21, 1993;365(6448):721-7.

Thompson et al., Precise nanometer localization analysis for individual fluorescent probes. Biophys J. May 2002;82(5):2775-83.

Thorne, Electrophoretic separation of polyoma virus DNA from host cell DNA. Virology. Jun. 1966;29(2):234-9.

Thuring et al., A freeze-squeeze method for recovering long DNA from agarose gels. Anal Biochem. May 26, 1975;66(1):213-20.

Ueno et al., Simple dark-field microscopy with nanometer spatial precision and microsecond temporal resolution. Biophys J. May 19, 2010;98(9):2014-23.

Van Oijen et al., Single-molecule kinetics of lambda exonuclease reveal base dependence and dynamic disorder. Science. Aug. 29, 2003;301(5637):1235-8.

Wiita et al., Force-dependent chemical kinetics of disulfide bond reduction observed with single-molecule techniques. Proc Natl Acad Sci U S A. May 9, 2006;103(19):7222-7. Epub Apr. 27, 2006.

Winfree et al., Design and self-assembly of two-dimensional DNA crystals. Nature. Aug. 6, 1998;394(6693):539-44.

Wong et al., The effect of integration time on fluctuation measurements: calibrating an optical trap in the presence of motion blur. Opt Express. Dec. 11, 2006;14(25):12517-31.

Yang et al., An integratable microfluidic cartridge for forensic swab samples lysis. Forensic Sci Int Genet. Jan. 2014;8(1):147-58. doi: 10.1016/j.fsigen.2013.08.012. Epub Sep. 8, 2013.

Yang et al., Multiplexed single-molecule force spectroscopy using a centrifuge. Nat Commun. Mar. 17, 2016;7:11026(1-7). doi: 10.1038/ncomms11026. PubMed PMID: 26984516; PubMed Central PMCID: PMC4800429.

Yang et al., Repurposing a Benchtop Centrifuge for High-Throughput Single-Molecule Force Spectroscopy. Methods Mol Biol. 2018;1665:353-366.

Zadeh et al., NUPACK: Analysis and design of nucleic acid systems. J Comput Chem. Jan. 15, 2011;32(1):170-3. doi: 10.1002/jcc.21596.

Zhang et al., Mechanoenzymatic cleavage of the ultralarge vascular protein, von Willebrand Factor. Science. Jun. 5, 2009;324(5932):1330-4.

Zheng et al., From molecular to macroscopic via the rational design of a self-assembled 3D DNA crystal. Nature. Sep. 3, 2009;461(7260):74-7. doi: 10.1038/nature08274.

U.S. Appl. No. 17/845,914, filed Jun. 21, 2022, Published, 2023-0045556.

U.S. Appl. No. 16/074,952, filed Aug. 2, 2018, Allowed, 2019-0048409.

U.S. Appl. No. 16/765,375, filed May 19, 2020, Granted, U.S. Pat. No. 11,591,636.

U.S. Appl. No. 18/168,131, filed Feb. 13, 2023, Pending.

Ahmad et al., New FRET primers for quantitative real-time PCR. Anal Bioanal Chem. Apr. 2007;387(8):2737-43. doi: 10.1007/s00216-007-1123-4. Epub Feb. 17, 2007.

Kenakin, Ligand detection in the allosteric world. J Biomol Screen. Feb. 2010;15(2):119-30. doi: 10.1177/1087057109357789. Epub Jan. 19, 2010.

Love et al., Observation of protein heptamer formation for chemically ligated early pregnancy factor. New methods for the Study of Biomolecular Complexes. 1998;171-9.

Meagher et al., Free-solution electrophoresis of DNA modified with drag-tags at both ends. Electrophoresis. May 2006;27(9):1702-12. doi: 10.1002/elps.200500554.

Wu et al., Detection of PCR amplicons from bacterial pathogens using microsphere agglutination. J Microbiol Methods. Mar. 2004;56(3):395-400. doi: 10.1016/j.mimet.2003.

* cited by examiner 1.2% AGE, 100V, 5h, SYBR Gold

NANOSWITCH CALIPER TRAINS FOR HIGH-THROUGHPUT, HIGH-RESOLUTION STRUCTURAL ANALYSIS OF BIOMOLECULES

RELATED APPLICATIONS

This application is a national stage filing under 35 U.S.C. § 371 of International Application No. PCT/US2021/020010, filed Feb. 26, 2021, which claims the benefit of the filing date of U.S. Provisional Application No. 62/983,648, filed on Feb. 29, 2020, the entire contents of each of which are incorporated by reference herein.

GOVERNMENT FUNDING

This invention was made with government support under GM119537 awarded by the National Institutes of Health and under N00014-20-1-2097 awarded by the Department of Defense Office of Naval Research. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Aug. 18, 2022, is named H049870715US01-SEQ-MAT and is 2,266 bytes in size.

FIELD OF INVENTION

The invention relates to and provides compositions, devices and methods for measuring intermolecular and intramolecular distances on a single-molecule basis.

BACKGROUND OF INVENTION

Proteins are the workhorses of the cell, assigned with many structural and functional purposes that are crucial for cell survival and function. To understand the biological tasks of proteins and refine insights into related disease mechanisms, detailed information about the tertiary structure of these macromolecules is required. Therefore, structural biology is an important area of research, consuming significant amounts of resources and equipment. Regardless of the success of high-resolution structure determination, the entire process remains complex and low-throughput. Additionally, the size and properties of a protein are often a limiting factor for obtaining sufficient high-resolution data. Computational algorithms that enable de novo protein-structure predictions try to overcome these challenges by calculating structural models based on the primary peptide sequence. Unfortunately, such models have shown limited success in replacing experimentally obtained structures.

Thus, while the ability to measure intramolecular distances in biomolecules such as proteins is important in proteomics and in structural analysis of biomolecules, currently available methods are relatively expensive, have low-throughput, and are not able to identify and determine the structure of biomolecules at the single-cell level. For example, mass spectrometry is not sensitive enough for single cell analysis and more importantly does not provide structural information of biomolecules. As another example, cryo-electron tomography is too noisy for biomolecule identification of heterogeneous samples and only provides low-resolution structural information.

SUMMARY OF INVENTION

The invention provides, inter alia, methods for high-throughput structure determination of a target of interest including macromolecules, such as proteins or complexes of proteins and/or nucleic acids. The methods involve measuring long-range distances between randomly selected points on the target of interest. These methods may be used to determine the structure of targets of known primary sequence or they may be used to solve the structure of a newly designed or isolated target. Furthermore, these methods may be used to identify targets based on their primary sequence.

Provided herein is a nucleic acid based nanodevice to measure distances between pairs of ssDNA handles displayed on the surface of biomolecules with high resolution and throughput. The disclosed method utilizes a covalently connected chain of single-stranded branched "T-junction" oligonucleotides strategically spaced apart by segments of defined length. An internal (e.g., middle) pair of T-junctions is used to incorporate target biomolecules, such as proteins, and the remaining T-junctions are used to display tracking or reporter moieties for reporting distance measurements. These nanodevices are able to accurately measure intramolecular distances to atomic resolution, a significant advance for proteomics and structural analysis of biomolecules.

The methods provided herein enable improved throughput and resolution of intramolecular distance measurements on individual biomolecules. No other methodology has heretofore achieved a degree of resolution on the order of what can be achieved with the disclosed nanodevices and methods of use. Furthermore, the use of reporter moieties such as nanoparticles may yield thousand- to million-fold higher throughput than conventional single-molecule instrumentation (e.g. dual-beam optical trap).

The new "T-series" architecture provided herein offers several advantages over earlier designs including: (1) tracking reporter moieties in series enables real-time force calibration; (2) an unbroken chain of covalent linkages for target-engaged calipers enables application of much higher pulling forces; (3) Nanoswitch Caliper Trains (NCT) can be stretched and captured on a separate apparatus than the microscope used for readout. Together these differences will enable more accurate measurements, and will allow parallel force application to thousands to millions of nanodevices per solid support (e.g., coverslip) simultaneously.

Accordingly, one aspect of this disclosure provides a composition comprising a nucleic acid having a plurality (2 or more) of single-stranded branched oligonucleotides, covalently attached to the nucleic acid using non-phosphodiester bonds, at pre-determined distances along its length.

The nucleic acid may be a Nanoswitch Caliper Car (NCC) or a Nanoswitch Caliper Train (NCT). If an NCC, the nucleic acid may be attached to additional NCC, at upstream and/or downstream positions.

In some embodiments, the nucleic acid is capable of being attached to a solid support (e.g., a coverslip) at its 3' and 5' ends. In some embodiments, the nucleic acid is attached to a solid support (e.g., a coverslip) at one end. In some embodiments, the nucleic acid is attached to a bead (e.g., a microbead) at one end. In some embodiments, the nucleic acid is attached to a bead at its 3' end and to a solid support at its 5' end, or vice versa.

In some embodiments, the nucleic acid is a DNA. In some embodiments, in the case of a NCC, the nucleic acid is 2 kb to 10 kb, or 2 kb to 5 kb, or 3 kb to 5 kb in length. In some embodiments, in the case of a NCT, the nucleic acid is 5 kb to 20 kb in length. In some embodiments, in the case of a NCT, the nucleic acid is 10 kb to 15 kb in length, including but not limited to about 13 kb in length. The nucleic acid may be longer, as the disclosure is not so limited.

In some embodiments, the branched oligonucleotides are DNA. In some embodiments, each of the branched oligonucleotides is 10-50 bases in length. In some embodiments, each of the branched oligonucleotides is about 30 bases in length. The branched oligonucleotides may of the same length or they be of differing lengths.

In some embodiments, a first subset of the branched oligonucleotides have identical nucleotide sequences. In some embodiments, a first subset of the branched oligonucleotides have non-identical nucleotide sequences.

In some embodiments, each of the first subset of the branched oligonucleotides is conjugated at its free end to a reporter moiety, optionally wherein all the reporter moieties on a nucleic acid are identical.

In some embodiments, a second subset of the branched oligonucleotides are not conjugated to a reporter moiety at their free end. In some embodiments, the second subset of the branched oligonucleotides have unique nucleotide sequences. In some embodiments, the second subset of the branched oligonucleotides have identical nucleotide sequences to each other.

In the case of an NCC, the plurality of branched oligonucleotides may be 2, 3 or 4, or more. In the case of an NCT, the plurality of branched oligonucleotides may be 2, 3, 4, 5, or 6 or more. In some embodiments, in the case of an NCT, the plurality of branched oligonucleotides is 6-10.

In some embodiments, the plurality of branched oligonucleotides is six, and four of the branched oligonucleotides have reported moieties on their free ends, and may have identical or non-identical nucleotide sequences, and two of the branched oligonucleotides do not have reporter moieties on their free ends, and may have unique nucleotide sequences.

Another aspect of this disclosure provides a method of attaching a protein to a nucleic acid. The method comprises contacting the nucleic acid of any of the foregoing compositions with a protein. The nucleic acid is a nucleic acid having a plurality of single-stranded branched oligonucleotides, covalently attached using non-phosphodiester bonds, at pre-determined distances along its length. The protein is a protein modified to have a plurality of single-stranded nucleic acid handles ("SS nucleic acid handles") on its surface or in an otherwise accessible location. The method further comprises attaching two adjacent internal branched oligonucleotides (from the nucleic acid) to two SS nucleic acid handles (from the protein), either covalently or non-covalently, thereby attaching the protein to the nucleic acid.

In some embodiments, the protein is attached to the nucleic acid by ligating (1) first and second SS nucleic acid handles to (2) first and second branched oligonucleotides respectively, wherein the first and second branched oligonucleotides are adjacent internal branched oligonucleotides.

In some embodiments, the protein is attached to the nucleic acid using (1) a first splint oligonucleotide that is partly complementary to the first SS nucleic acid handle and partly complementary to the first branched oligonucleotide, and (2) a second splint oligonucleotide that is partly complementary to the second SS nucleic acid handle and partly complementary to the second branched oligonucleotide.

In some embodiments, the first splint oligonucleotide is hybridized to the first SS nucleic acid handle and the first branched oligonucleotide and the second splint oligonucleotide is hybridized to the second SS nucleic acid handle and the second branched oligonucleotide.

In some embodiments, the method further comprises contacting the nucleic acid with the protein in the presence of a ligase.

In some embodiments, the protein is incorporated into the nucleic acid by hybridizing (1) first and second SS nucleic acid handles to (2) first and second branched oligonucleotides respectively, wherein the first and second branched oligonucleotides are adjacent internal branched oligonucleotides, wherein the first and second SS nucleic acid handles are partly or fully complementary the first and second branched oligonucleotides respectively.

In some embodiments, the SS nucleic acid handles are attached to identical amino acids in the protein. In some embodiments, the SS nucleic acid handles are attached to cysteines in the protein. In some embodiments, the SS nucleic acid handles are attached to lysines in the protein. In some embodiments, a first subset of SS nucleic acid handles is attached to a first amino acid and a second subset of SS nucleic acid handles is attached to a second amino acid. The first and second subsets may be of equal proportion (about 50% and about 50%) or they may be disproportionate (e.g., 5% and 95% or 10% and 90% or 25% and 75%).

Another aspect of this disclosure provides a composition comprising a nucleic acid-protein complex comprising a nucleic acid having a plurality of single-stranded branched oligonucleotides, covalently attached using non-phosphodiester bonds, at pre-determined distances along its length, a first subset of branched oligonucleotides having reporter moieties at their free ends, and a protein attached to two adjacent, internal branched oligonucleotides that do not have reporter moieties at their free ends.

Another aspect of this disclosure provides a method of performing distance measurements of a protein, comprising (1) providing a nucleic acid-protein complex comprising
    a nucleic acid having a plurality of single-stranded (SS) branched oligonucleotides (e.g., six branched oligonucleotides denoted T1-T6), covalently attached using non-phosphodiester bonds, at pre-determined distances along the length of the nucleic acid, a first subset of branched oligonucleotides having reporter moieties at their free ends (e.g., those denoted T1, T2, T5, T6), and
    a protein having first and second single-stranded (SS) nucleic acid handles attached to first and second adjacent, internal branched oligonucleotides (e.g., denoted T3, T4),
    wherein a first end of the nucleic acid is attached to a solid support (e.g., a coverslip) and a second end of the nucleic acid is attached to a bead (e.g., a microbead),
(2) applying a force on the nucleic acid-protein complex in the direction of the bead, and
(3) detecting location of the first subset of branched oligonucleotides (or reporter moieties) under force, optionally relative to location of the first subset of branched oligonucleotides (or reporter moieties) in the absence of force, and/or
    measuring distance between adjacent reporter moieties under force, optionally relative to distance between adjacent reporter moieties in the absence of force, wherein a change in location or a change in distance represents a distance between the first and second SS nucleic acid handles.

In some embodiments, the nucleic acid-protein complex comprises four branched oligonucleotides, two of which are attached to reporter moieties and flank (i.e., are positioned on both sides of) the remaining two which are attached to SS nucleic acids on the protein. The nucleic acid-protein complex may comprise additional branched oligonucleotides, including for example another two which are attached to reporter moieties and flank the four branched oligonucleotides on both sides. The method may comprise detecting and/or measuring changes in distance between the two reporter moieties that immediately flank the branched oligonucleotides attached to the protein SS nucleic acid handles. The method may further comprise detecting and measuring changes in distances between a pair of reporter moieties that are adjacent to each other and located either upstream or downstream of the protein.

Another aspect of this disclosure provides a method of performing distance measurements of a protein, comprising providing a nucleic acid-protein complex comprising (1) a nucleic acid covalently attached using non-phosphodiester bonds, at pre-determined distances along its length, to five single-stranded branched oligonucleotides (T1-T5), the first, second and fifth branched oligonucleotides (T1, T2, T5) having reporter moieties at their free ends, and (2) a protein having first and second single-stranded nucleic acid handles (SS nucleic acid handles) attached to the third and fourth branched oligonucleotides (T3, T4), wherein a first end of the nucleic acid is attached to a solid support and a second end of the nucleic acid is attached to a bead, applying a force on the complex in the direction of the bead, and (i) detecting the location of the reporter moieties attached to T2 and T5 and optionally T1 under force, optionally relative to their location in the absence of force, and/or (ii) measuring distance between reporter moieties attached to T2 and T5 and optionally T1 under force, optionally relative to said distance in the absence of force, wherein a change in location or a change in distance under force represents a distance between the first and second SS nucleic acid handles on the protein.

In some embodiments, the method further comprises detaching the fourth branched oligonucleotide (T4) from the second SS nucleic acid handle, attaching the fourth branched oligonucleotide to a third SS nucleic acid handle on the protein, re-applying a force on the complex in the direction of the bead, and performing (i) and/or (ii), wherein a change in location or a change in distance under force represents a distance between the first and third SS nucleic acid handles on the protein.

Another aspect of this disclosure provides a method of performing distance measurements of a protein, comprising providing a nucleic acid-protein complex comprising (1) a nucleic acid covalently attached using non-phosphodiester bonds, at pre-determined distances along its length, to five single-stranded branched oligonucleotides (T1-T5), the first, fourth and fifth branched oligonucleotides (T1, T4, T5) having reporter moieties at their free ends, and (2) a protein having first and second single-stranded nucleic acid handles (SS nucleic acid handles) attached to the second and third branched oligonucleotides (T2, T3), wherein a first end of the nucleic acid is attached to a solid support and a second end of the nucleic acid is attached to a bead, applying a force on the complex in the direction of the bead, and (i) detecting the location of the reporter moieties attached to T1 and T4 and optionally T5 under force, optionally relative to their location in the absence of force, and/or (ii) measuring distance between reporter moieties attached to T1 and T4 and optionally T5 under force, optionally relative to said distance in the absence of force, wherein a change in location or a change in distance under force represents a distance between the first and second SS nucleic acid handles on the protein.

In some embodiments, the method further comprises detaching the third branched oligonucleotide (T3) from the second SS nucleic acid handle, attaching the third branched oligonucleotide to a third SS nucleic acid handle on the protein, re-applying a force on the complex in the direction of the bead, and performing (i) and/or (ii), wherein a change in location or a change in distance under force represents a distance between the first and third SS nucleic acid handles on the protein.

Another aspect of this disclosure provides a method of performing distance measurements of a protein, comprising providing a nucleic acid-protein complex comprising (1) a nucleic acid covalently attached using non-phosphodiester bonds, at pre-determined distances along its length, to six single-stranded branched oligonucleotides (T1-T6), the first, second, fifth and sixth branched oligonucleotides (T1, T2, T5, T6) having reporter moieties at their free ends, and (2) a protein having first and second single-stranded nucleic acid handles (SS nucleic acid handles) attached to the third and fourth branched oligonucleotides (T3, T4), wherein a first end of the nucleic acid is attached to a solid support and a second end of the nucleic acid is attached to a bead, applying a force on the complex in the direction of the bead, and (i) detecting the location of the reporter moieties attached to T1, T2, T5 and T6 under force, optionally relative to their location in the absence of force, and/or (ii) measuring distance between reporter moieties attached to T1, T2, T5 and T6 under force, optionally relative to said distance in the absence of force, wherein a change in location or a change in distance under force represents a distance between the first and second SS nucleic acid handles on the protein.

In some embodiments, the method further comprises detaching the fourth branched oligonucleotide (T4) from the second SS nucleic acid handle, attaching the fourth branched oligonucleotide to a third SS nucleic acid handle on the protein, re-applying a force on the complex in the direction of the bead, and performing (i) and/or (ii), wherein a change in location or a change in distance under force represents a distance between the first and third SS nucleic acid handles on the protein.

It is to be understood that either of the branched oligonucleotides conjugated to SS nucleic acid handles may be cleaved, using any available methodology (e.g., sequence specific endonucleases). It is also to be understood that the SS nucleic acid handles may be attached to the same amino acid (e.g., all attached to cysteines or all attached to lysines) or they may be attached to two or more amino acids. If the latter, typically the SS nucleic acid handles that bind to a first amino acid (e.g., cysteine) are different from those that bind to a second amino acid (e.g., lysine).

These and other aspects and embodiments provided herein are described in greater detail herein.

BRIEF DESCRIPTION OF DRAWINGS

FIG. 4A: L: 1 kb DNA ladder; 1: No ligation splints present; 2: Ligation splint s1 present; 3: Ligation splint s2 present; 4: Both ligation splint, s1 and s2, are present. Only in this case we observed a gel shift of the NCC, indicating the successful capture and ligation of the peptide to NCC v2.1.

DETAILED DESCRIPTION OF INVENTION

Figure 1:
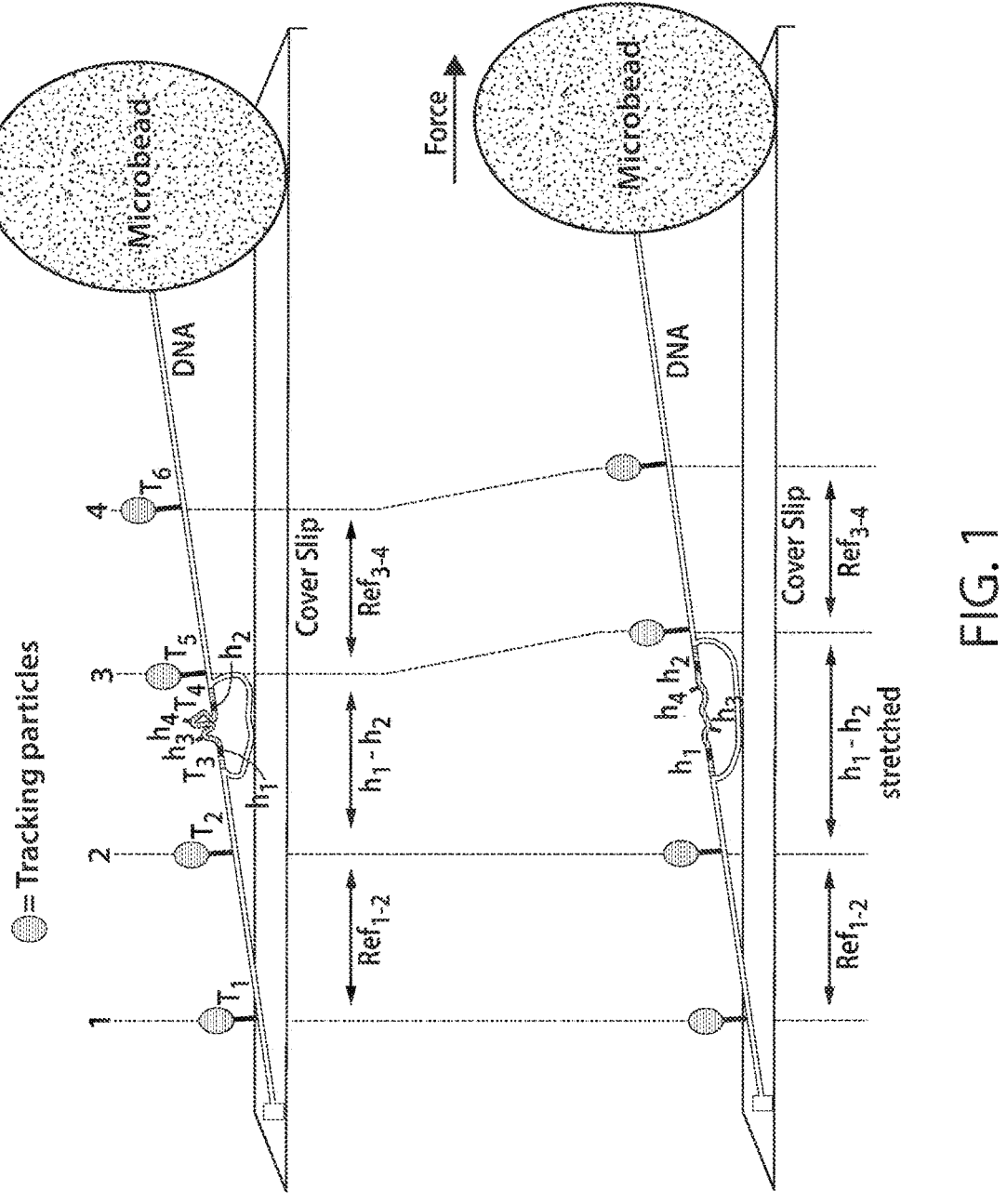
FIG. 1. Schematic of a Nanoswitch Caliper Train (NCT) as a nucleic acid (e.g., DNA) strand with six "T-junctions" in series. Each NCT is attached covalently on its rear to a solid support such as a coverslip and on its front to a bead such as a microbead. A uniform force can be applied on command to all beads using for example laterally directed flow or centrifugation for extension of the NCT at a small angle away from the coverslip surface, while adhesion between DNA-extensions on the microbead and coverslip can be reversibly actuated by introduction versus removal of bridging strands. The embodiment illustrates the use of 6 T junctions but it is to be understood that fewer (e.g., 5) or more (e.g., 7 or more) are also contemplated and embraced by this disclosure.

The methods provided herein are used to determine structural features including complete 3D structure of targets of interest. Such targets include without limitation proteins, multiprotein complexes, protein-nucleic acid complexes, and the like. Any target that can be surface modified through attachment to nucleic acids, in a directed (i.e., non-random manner) can be analyzed according to the methods provided herein.

The methods provided herein generally involve monitoring and/or measuring distances between reporter moieties on a nucleic acid that is complexed to a biomolecule of interest, such as a protein, wherein the reporter moieties flank the protein. The nucleic acid-biomolecule (e.g., nucleic acid-protein) complex is designed such that upon application of force, the biomolecule is able to extend and the reporter moieties that flank the protein are able to move away from each other by a distance that is indicative of the degree of stretch in the protein. Various aspects, embodiments and examples are provided relating to proteins, but it is to be understood that the disclosure contemplates and embraces other targets provided they can be attached to SS nucleic acid handles.

Accordingly, certain methods provided herein stretch individual targets such as proteins and multi-protein complexes with nucleic acid nanodevices, and measure the distances of such nanodevices upon stretching using high-throughput, high-resolution means such as but not limited to centrifugal force microscopy or laterally directed flow (e.g., flow cells). Importantly, the methods can be performed on a single-molecule level and thus are not hindered by a bulk population analysis of certain existing methods.

This disclosure provides nanodevices, referred to herein as Nanoswitch Caliper Trains (NCTs), to be used for high-throughput biomolecule identification and structural characterization with atomic resolution using long-range intramolecular distance measurements. These nucleic acid-based devices are capable of measuring distances between labeled points of interest on the surface of individual biomolecules such as proteins. The binding and unbinding of these calipers to different locations on the biomolecule surface and the tracking of reporter moieties such as nanoparticles along the device allow for the reconstruction of a three-dimensional virtual mesh that encloses the structure of the biomolecule. NCTs can operate on a shared solid support such as a glass coverslip, thereby offering the ability to analyze thousands to millions of biomolecules simultaneously. Overall, these devices will provide unparalleled structural information of biomolecules and their complexes at the single-molecule level.

Herein, we combine nucleic acid nanotechnology with high-throughput single-molecule manipulation to create a Nanoswitch Caliper Train system (NCTs), which is designed to acquire experimental protein structural data in a simple and high-throughput manner.

The NCT system will leverage the sensitivity and flexibility of dynamic nucleic acid nanostructures that will allow subnanometer distance measurements to be made between pairs of nucleic acid (e.g., ssDNA) handles displayed on the surface of "target" biomolecules such as proteins. A randomly selected pair of "target" handles loops out a segment of a long DNA "nanoswitch caliper" and thereby reduces the caliper's full-extension length. Recently, we demonstrated calibrated readout of the end-to-end distance of a caliper prototype, actuated by a dual-beam optical trap, down to subnanometer-resolution; after averaging over multiple attachment/detachment cycles, angstrom resolution could be recovered.

Here we report the fabrication of an NCT prototype. The key innovation of constructing each NCT is a "T series", a covalently connected chain of six single-stranded "T-junctions" (FIG. 1, indicated as T1-T6), spaced by nucleic acid (e.g., DNA) segments of defined length. The middle pair of T-junctions (FIG. 1, T3 and T4) can be used for attachment (e.g., covalent ligation, hybridization, etc.) to target handles (FIG. 1, h1-h4). The other four T-junctions (FIG. 1, T1, T2, T5, and T6) can be functionalized (e.g. covalent ligation, hybridization, etc.) with a reporter moiety such as a reporter particle (RP) for tracking purposes. Examples of suitable reporter moieties include but are not limited to gold nanoparticles (AuNPs), quantum dots, fluorophores, and DNA origami structures. The methods involve measuring the separation between the central pairing of RP, typically under force, as a surrogate measure of the change in the length of the target which such RPs flank. Simultaneous measurements of the separations between the peripheral pairings of RPs (T1 and T2 and/or T5 and T6) can be used for real-time calibration.

This "T-series" architecture offers several advantages. First, the ability to track reporter moieties on the same device in series enables real-time force calibration. Second, use of an unbroken chain of covalent linkages for target-engaged calipers enables application of much higher pulling forces than was previously possible. Third, NCTs can be stretched and captured on a separate apparatus than the microscope used for readout. These innovations will result in more accurate measurements, and will enable parallel force application to thousands to millions of calipers per solid support such as a coverslip simultaneously.

These single-particle measurements will reveal unprecedented levels of detail on static and dynamic heterogeneity of proteins, and these datasets will prove invaluable for elucidating their structural characterization. More generally, these caliper measurements will revolutionize single-molecule structural analysis of a broad spectrum of biomolecular particles, both natural and synthetic (e.g. peptides, multiprotein complexes, DNA-protein complexes, etc.)

Nanoswitch Caliper Trains (NCTs)

The rationale of NCTs and their use is described briefly. A biomolecule, such as a protein, is fastened at two of its surface residues to a nucleic acid, sometimes referred to herein as a nanoswitch caliper train (NCT). The nucleic acid is itself attached at one end to a solid support such as a surface (e.g., a coverslip) and at the other end to a bead such as a microbead. A force is applied to the bead in order to extend the NCT. Such force may be centrifugal force, gravitational force, magnetic force, or laterally directed flow, etc.

The NCT therefore comprises a nucleic acid (e.g., DNA) strand that is covalently attached to a series of single-stranded branched oligonucleotides (also referred to herein as T junctions). These oligonucleotides are attached to the nucleic acid "backbone" through non-phosphodiester linkages, giving rise to a branched configuration. A pair of consecutive (adjacent) branched oligonucleotides that are internally situated on the nucleic acid backbone (i.e., there are at least 1 or 2 other T junctions that flank this pair both upstream and downstream along the nucleic acid backbone) are used to capture (or bind) the biomolecule of interest (e.g., a protein). The remaining flanking T junctions are typically conjugated to a reporter moiety such as a reporter particle or other detectable moiety at their free ends. The position of the reporter moieties, and the distance between adjacent reporter moieties, are detected, monitored and/or measured as force is applied to the NCT.

In an illustrative example, the NCT comprises 6 T junctions (T1-T6). T1, T2, T5 and T6 are all conjugated to reporter moieties. T3 and T4 are used to capture the biomolecule of interest and are located in series between T2 and T5. The distance between T2 and T5 under force is therefore indicative of the distance between two randomly bound positions in the biomolecule. The distance between T1 and T2 or between T5 and T6, on the other hand, is used to perform real-time force calibration on the same NCT. The change in distance between T2 and T5 is illustrated in FIG. 1 (albeit T5 and T6 are labeled 3 and 4). The reporter moiety is represented by a tracking particle, and the NCT is attached on one end to a solid support such as a coverslip, and on the other end to a microbead.

The biomolecule of interest is captured by T3 and T4 at respective single stranded nucleic acid handles h1 and h2. The Figure further illustrates that the biomolecule comprises other handles, namely h3 and h4, that are not engaged by T3 and T4. The capture of the biomolecule may be accomplished in any number of ways including for example by ligating T3 to h1 and ligating T4 to h2 or by hybridizing T3 to h1 and hybridizing T4 to h2 or by hybridizing T3 and h1 to a "splint" oligonucleotide and hybridizing T4 and h2 to another splint oligonucleotide. If ligation is used, a splint oligonucleotide that is partly complementary to T3 and partly complementary to h1 may be used to bring these oligonucleotides together sufficiently for ligation to occur. Similarly, a splint oligonucleotide that is partly complementary to T4 and partly complementary to h2 may be used to bring these oligonucleotides together sufficiently for ligation to occur.

Once the biomolecule is captured, a loop is created in the nucleic acid "backbone" because the length of the biomolecule when not under tension is typically less than the length between T3 and T4 in the backbone. However, even when the biomolecule is stretched under force, typically the backbone will still appear looped. This is partly due to the design of the NCT, which sets the T junctions (branched oligonucleotides) sufficiently apart from each other such that this distance is always greater than the distance between any two randomly selected positions on the biomolecule.

When force is applied, the distance between h1 and h2 increases, as does the distance between T2 and T5. This is illustrated in FIG. 1.

In addition to measuring the distance between two randomly selected positions in the biomolecule, the NCTs can be used to map the biomolecule. This may be accomplished in a number of ways. In one exemplary embodiment, T3 binds to h1 and T4 binds to h2, and the distance between T2 and T5 is measured under force. Then the bond between T4 and h2 may be cleaved and T4 may be allowed to bind to another handle on the biomolecule. Accordingly, T4 may next bind to h3 and the process is repeated (i.e., force is applied to the NCT and the distance between T2 and T5 is measured). One of skill will readily appreciate that this process may be repeated until the biomolecule is sufficiently mapped. It should also be apparent that once mapping is complete keeping the T3/h1 bond intact, then mapping may be extended by keeping the T4/hx bond intact and cleaving the T3/h1 bound instead.

As described herein, the NCT is typically comprised of nucleic acids (i.e., the nucleic acid backbone and the branched oligonucleotides). These may be DNA but are not so limited. The backbone may range in length from 5 kb to 20 kb, although it is not so limited. In some embodiments, it may be about 10-15 kb, including about 13 kb. The backbone may be single or double stranded (e.g., ssDNA or dsDNA).

The branched oligonucleotides may be 10-50 bases in length, although they are not so limited. In some embodiments, they may be about 25-35 bases in length, including about 30 bases in length. The nucleotide sequences of the branched oligonucleotides bearing the reporter moieties are typically identical to each other, as is their length, but they are not so limited. Alternatively, branched oligonucleotides can be of unique sequence and of different lengths. The nucleotide sequences of the branched oligonucleotides that capture the biomolecule are typically unique (i.e., different from each other and different from the remaining, flanking, reporter-bearing branched oligonucleotides), but can alternatively be identical.

The biomolecule of interest has been modified to comprise single-stranded nucleic acid handles at non-random positions. For example, in the case where the biomolecule is a protein, such protein may comprise single-stranded nucleic acids at surface cysteines or at surface lysines, or at both surface cysteines and surface lysines, etc. The distance between T2 and T5 under force therefore indicates the distance between two cysteines, two lysines, or one cysteine and one lysine on the protein, for example.

The disclosure contemplates a scenario where the location of one or both attachment points are known. For example, the attachment points may be two particular residues, the positions of which in the primary structure of a protein are known.

The disclosure also contemplates a scenario where the attachments are made at residues of a known type but unknown position. For example, the attachment points may be two lysines (due to the attachment chemistry used) but the positions of these lysines in the primary amino acid sequence of the target protein are unknown. In other words, in some instances, the attachment points will be lysines but which particular lysines in the target protein will not be known.

Biomolecules to be analyzed are modified at specific sites through the attachment of single-stranded nucleic acid handles (which may be referred to herein as ssDNA "handles", for brevity and as an example). The sites may be a subset of sites on the surface of the target (e.g., all surface lysines).

The method is used to measure the distance between these ssDNA "handles" attached to two sites on a target protein. The handles may be attached to the target protein using a variety of chemistries, each of which has amino acid specificity. As an example, two randomly selected lysines on the surface of a target protein react with NHS-functionalized oligonucleotides, to form a target protein having two ssDNA handles attached to random lysines that are surface accessible. Similarly, other chemistries can be used to attach to other surface residues. For example, thiol-specific reagents can be used to attach to cysteines, amine-specific reagents can be used to attach to an amino-terminus of a protein or to lysines), carboxyl-specific reagents can be used to attach to a carboxy-terminus of a protein or to aspartates or glutamates, guanidine-specific reagents can be used to attach to arginines, imidazole-specific reagents can be used to attach to histidines, phenol-specific reagents can be used to attach to tyrosines, indole-specific reagents can be used to attach to tryptophans, amino-terminus specific reagents can be used to attach to the amino terminus of a protein, and carboxy-terminus specific reagents can be used to attach to the carboxy terminus. Basle et al., Protein chemical modification on endogenous amino acids. Chem Biol. 17, 213-227, 2010 describes such various chemistries, and is incorporated by reference herein.

Heterobifunctional crosslinkers can be used to facilitate the attachment of ssDNA handles by using a multi-step process. For example, first modifying specific residues on a target protein with a heterobifunctional crosslinker and then attaching the oligonucleotide to the modified target protein. Similarly, this process (or order) can be reversed and the oligonucleotide may be first modified with a heterobifunctional crosslinker, etc.

As will be understood based on this disclosure, for monomeric targets such as monomeric proteins, cysteine engineering of the target is not required. However, an intermediate handle-tagging approach could be used that involves the generation of targets having single cysteine mutants, and then attachment of one maleimide-ssDNA handle (specific for the cysteine mutant) and one NHS-ssDNA handle (specific for lysine) to each of those targets. Any other chemically labile positions on the target (e.g., amino terminus or tyrosines, for example, in the context of a target protein) can be used as attachment points for the ssDNA handles. Reference can be made to Baslé et al., Protein chemical modification on endogenous amino acids. Chem Biol. 17, 213-227, 2010 for reactive moieties or groups that may be used to target various residues in a target protein.

The microbead may have a diameter of 1-3 microns, although it is not so limited.

The reporter moiety may be a reporter particle or tracking particle that is on the order of 5-40 nm in diameter, although not so limited.

Producing Linear Nanoswitch Caliper Cars (NCCs) and Nanoswitch Caliper Trains (NCT)

Construction of a fully functional Nanoswitch Caliper Train (NCT) involves incorporating a plurality of T-junctions into a long nucleic acid strand. In an exemplary embodiment, six single-stranded nucleic acid (e.g., DNA) T-junctions are incorporated into a long nucleic acid (e.g., DNA) strand. The T-junctions are oligonucleotides attached, typically covalently attached, to the long nucleic acid using non-phosphodiester linkages. Such T-junctions are referred to herein as "branched oligonucleotides". These T-junctions are spaced along the long nucleic acid strand in a pre-determined manner, typically spaced apart by up to three thousand nucleotides, although not so limited. NCTs were synthesized using modular units referred to as Nanoswitch Caliper Cars (NCCs), which are ligated together in a specific or programmed manner to form a fully covalent NCT device or system. These systems are able to withstand higher pulling forces as compared to previous caliper designs and are thereby able to stretch biomolecules such as proteins to their full contour length.

An exemplary synthesis of the modular NCC units is outlined in FIG. 2A-D. The synthesis starts from a ~5 kb double-stranded, circular DNA plasmid, consisting of a commercially-available segment and an insert, with two uniquely designed nicking cassettes. The nicking cassettes varied in the distance they were spaced apart from each other. Each of the two cassettes was processed with three nicking enzymes, which targeted a specific site, spaced seven base pairs apart from one another. The combined action of the nicking enzymes generated short 7mer sequences within the double stranded plasmid (FIG. 2A-D, 1) and allowed for the dissociation of the 7mers and hybridization of a 14mer T-junction to each nicking cassette (FIG. 2A-D, 2+3). The replacement T-junctions were prepared beforehand as a click-chemistry-conjugate between an oligonucleotide end-labeled with an azide functional group and a 14mer oligonucleotide with a modified dU bearing an alkyne functional group on the C5 of the pyrimidine ring. Importantly, each nicking cassette was designed to be unique in its sequence context and complementary to a specific 14mer sequence of a specific T-junction, thus allowing for the strategic incorporation of different DNA handle functionalities into each cassette.

Figure 2A:
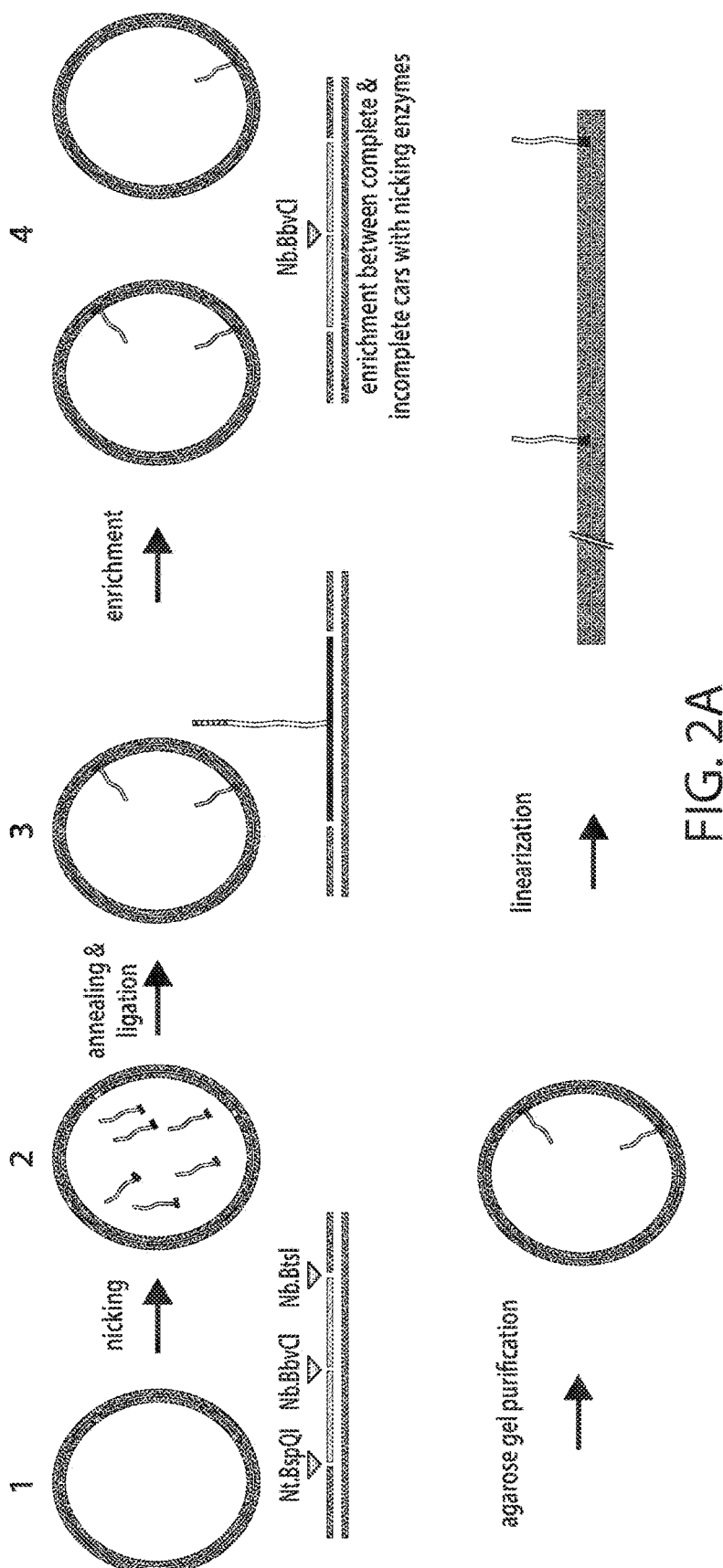
FIG. 2A. General overview of an exemplary Nanoswitch Caliper Car (NCC) construction scheme. The starting material for all NCCs is a circular double-stranded plasmid that contains two nicking cassettes (1) and into which T-junctions can be inserted (2+3). Enrichment (4) ensures only use of NCCs that have all T-junctions for the subsequent construction of the NCT. Further this step also allows for agarose gel purification of complete versus incomplete NCCs (5). Finally, restriction enzymes are used to linearize the circular NCC, which then can be used for the construction of the NCT.
Figures 2B, 2C:
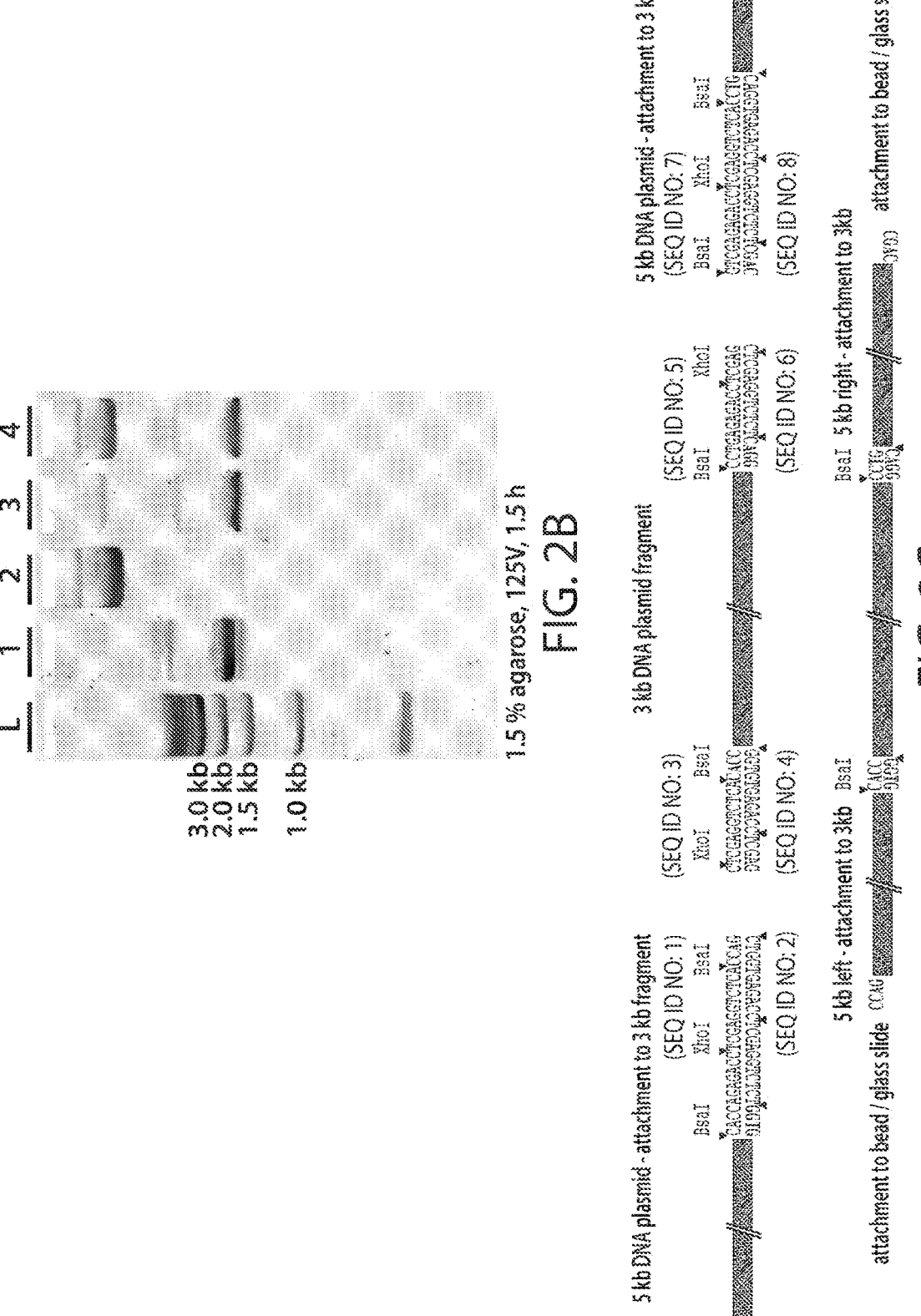
FIG. 2B. Gel analysis of the individual NCC fabrication steps. L: 1 kb DNA ladder; 1: Circular plasmid; 2: Nicked cassettes; 3: Ligated T-junctions; 4: Enrichment with Nb.BbvCI.
FIG. 2C. The restriction enzymes create unique 4-base overhangs, that allow for specific ligations of the three NCC's to one 13 kb NCT.
Figure 2D:
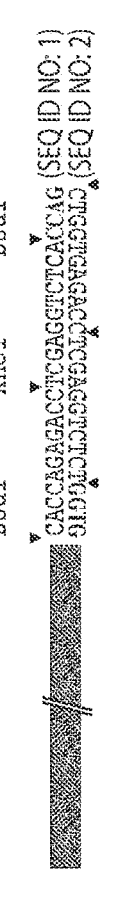
FIG. 2D. Expanded views of the constructs provided in FIG. 2C along with the nucleotide sequences of the relevant ends.
Figure 2D:
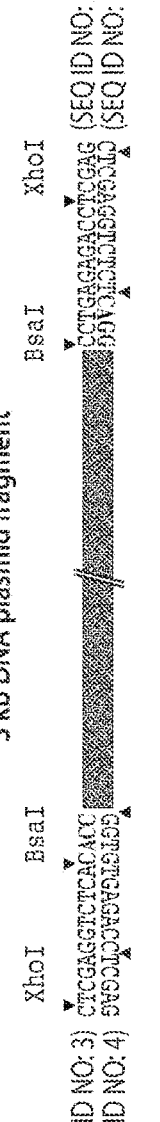
Figure 2D:
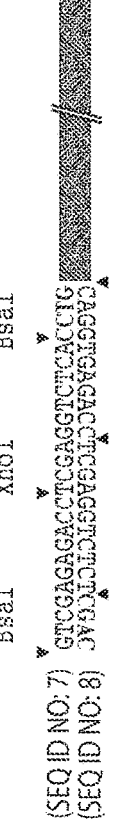

The incorporation of the T-junctions was validated by an enrichment step, which allowed for the removal of NCCs with empty nicking cassettes. Basis for the enrichment step formed the design of the nicking cassettes which upon incorporation of a T-junction were inaccessible for the "middle" nicking enzyme and inhibited its activity. Thus, the plasmid was only nicked in the absence of a T-junction (FIG. 2A (4)). We have validated each of these individual steps by agarose gel electrophoresis shown in FIG. 2B. The complete NCCs could then be purified with agarose gel electrophoresis due to the different mobility of nicked (incomplete) and un-nicked (complete) NCCs (FIG. 2B, lane 4, the top band represent the nicked plasmids whereas the lower band represents the un-nicked, complete, NCCs). As a last step, the circular NCCs were then linearized with specific restriction enzymes which generated unique 4-base overhangs, that offer the possibility to specifically ligate the three individual NCCs to one 13 kb NCT (FIG. 2C).

Ligation of Multiple NCCs to One NCT

Figure 3A:
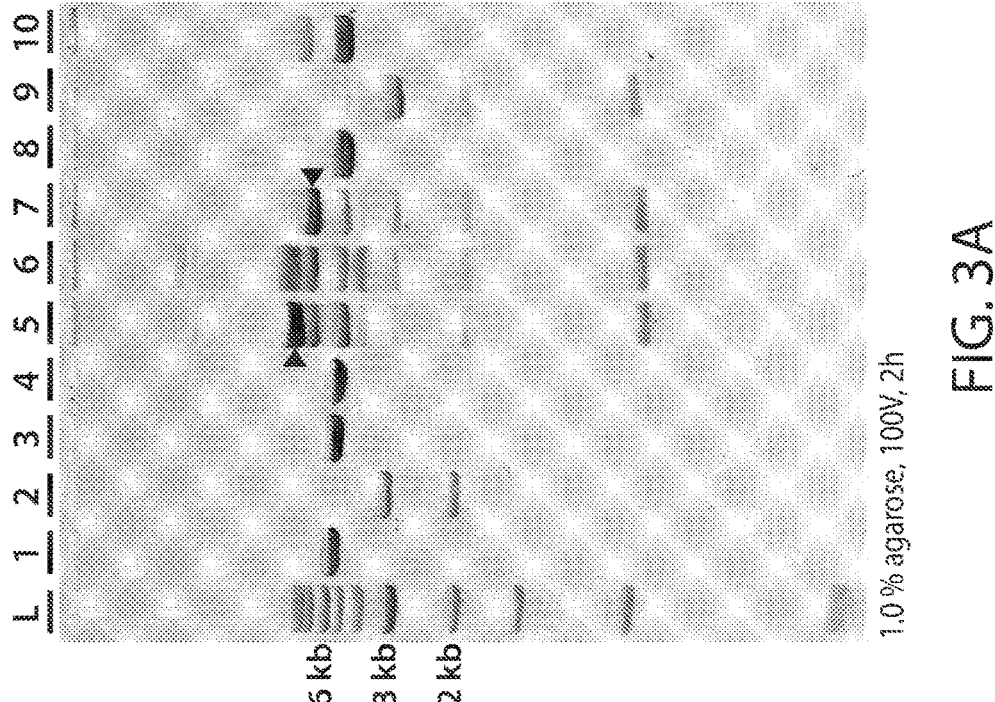
FIGS. 3A-3B. Programmable assembly of multiple NCCs to one NCT. L: 1 kb DNA ladder; 1: Linearized 5 kb plasmid v2.0; 2: Linearized 5 kb plasmid v2.1; 3: Linearized 5 kb plasmid v2.2; 4: Column purified linear plasmid; 5: Full length NCT construct, consisting of NCC v2.0, v2.1, and v2.2 ligated together; 6: Ligation of NCC v2.0 with v2.1; 7: Ligation of NCC v.2.1 with v.2.2; 8: NCC v2.0 w/T4 DNA ligase; 9: NCC v2.1 w/T4 DNA ligase; 10: NCC v2.2 w/T4 DNA ligase.
Figure 3B:
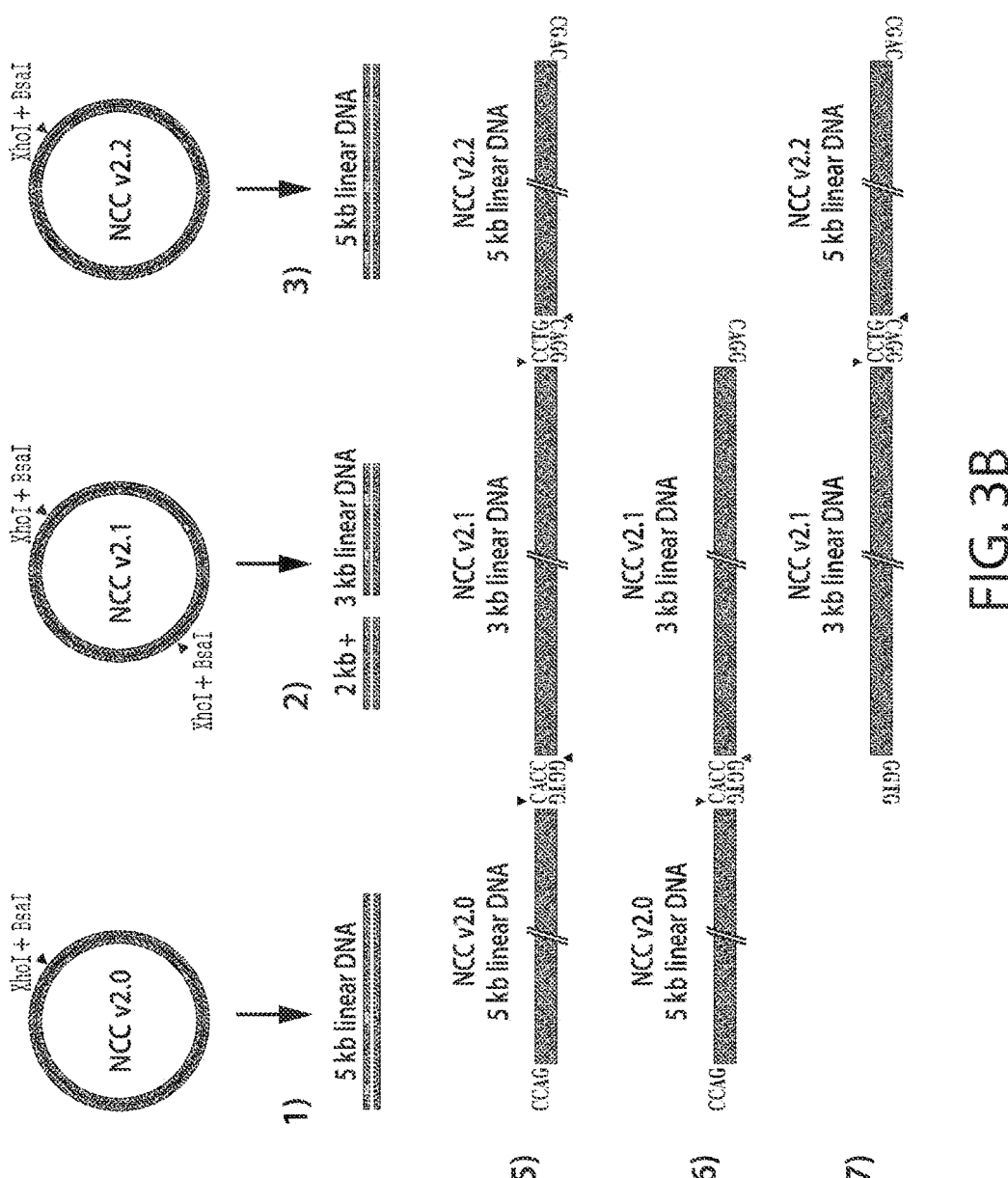

An exemplary full length NCT prototype was built by a serial ligation of up to 3 NCCs, to generate a long, DNA tether, with a defined order of T-junctions. In order to facilitate the assembly of multiple NCCs and make it as programmable as possible, three different plasmid version—v2.0, v2.1, and v2.2—were used, which allow for the creation of unique 4-base overhangs during the restriction digest outlined in FIG. 2C. We have validated that the restriction digest runs to completion (FIG. 3A, lane 1, 2, and 3) and created the desired linear 5 kb, and 3 kb fragments. The linear fragments could then be combined and ligated together with T4 DNA ligase, resulting in the full length NCT construct with a total length of ~13 kb (FIG. 3A, lane 5). Importantly, we could also verify that the linear constructs only generate marginal amounts of background, i.e. self-ligation, upon treating the linear fragments with T4 DNA ligase (FIG. 3A, lane 8, 9, and 10).

Validation of the T-Junction Functionality

Figure 4A:
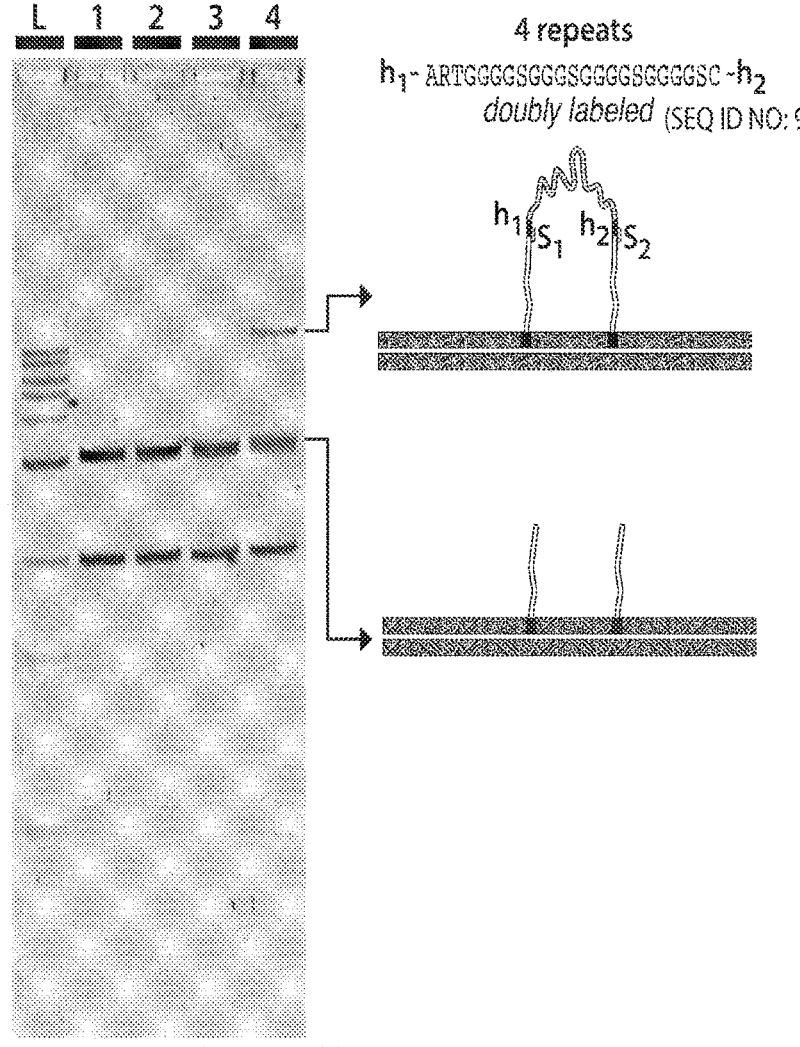
FIGS. 4A and B. Gel analysis of the peptide capturing experiments.

After the successful fabrication of the NCC's, the functionality of the T-junction handles was validated with exemplary peptide ligation experiments. Therefore, NCCs with two analyte attachment handles were combined with a DNA-labeled peptide. Complementary splints were used to anneal the labeled peptide to the DNA attachment handles on the NCC, which subsequently were ligated with T4 DNA ligase. In the case where two splints were present and both DNA attachment handles were ligated, the NCC formed a looped-out-structure, which could be observed by a slower gel mobility on an agarose gel (FIG. 4A, lane 4) and indicated that the ligation of the peptide to the NCC was successful.

Figure 4B:
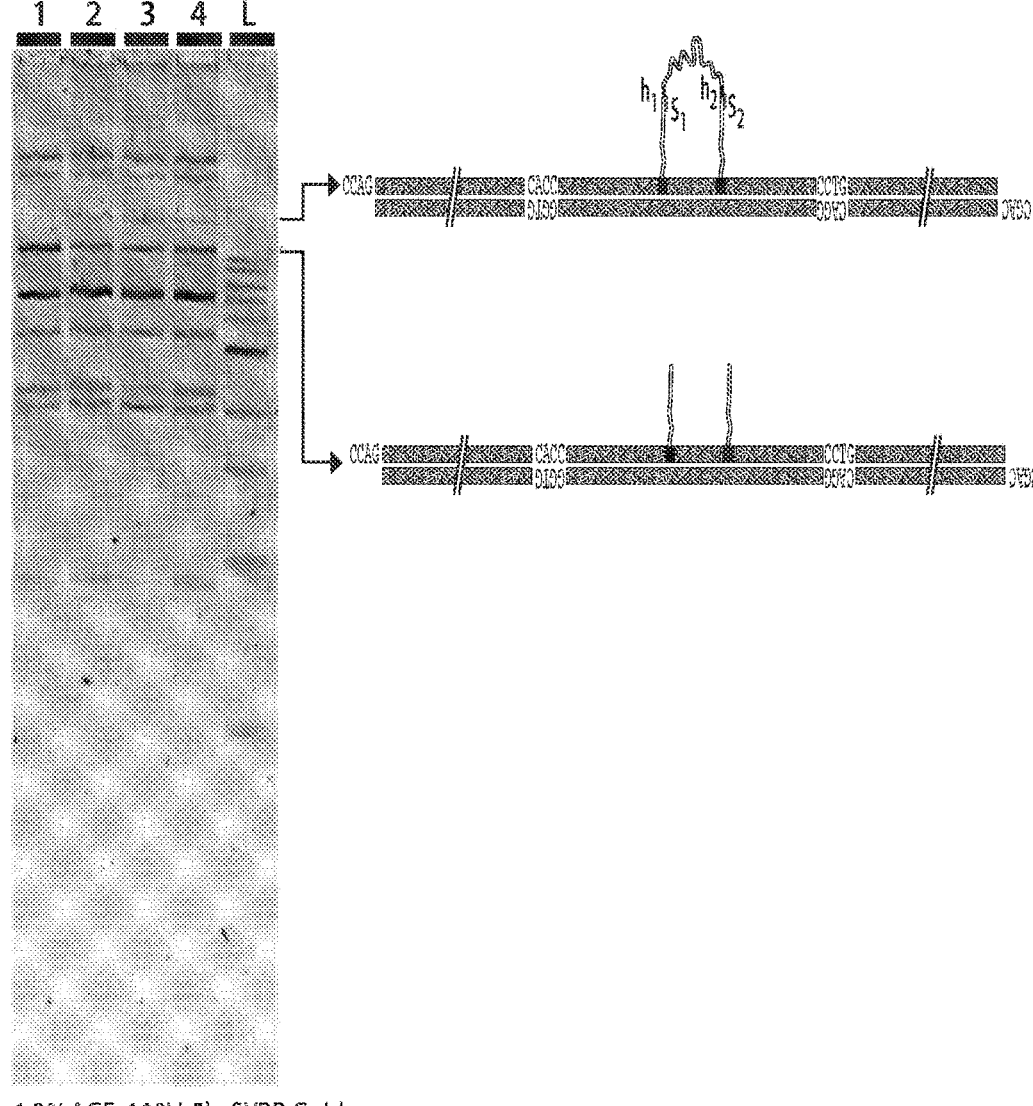
FIG. 4B: 1: No peptide present; 2: Peptide and 5 equiv. ligation splints, s1 and s2, are present; 3: Peptide and 10 equiv. ligation splints, s1 and s2, are present; 4: Peptide and 20 equiv. ligation splints, s1 and s2, are present; L: 1 kb DNA ladder.

In addition, we also assessed the incorporation of the DNA-labeled peptide into the full NCT. The 3 NCCs were ligated together and the DNA-labeled peptide was incorporated into the NCT in the same reaction mixture. Gel results showed a clear gel mobility shift when the peptide was present with the 3 NCCs and varying concentrations of splints (FIG. 4B, lane 2-4).

Nanoparticle Tracking for Distance Measurements on an Analyte

An important feature of the NCT system lies in the anticipated tracking of nanoparticles instead of following the movement of a large microbead for distance measurements. The modularity of the NCT system allows for the placement of a number of nanoparticles in series on the NCT. This feature is crucial for real-time force calibration, which means that any non-uniform force on thousands to millions of NCTs will not affect the accuracy of the measurement. In addition, the internal references also open up the possibility to stretch and capture the NCTs on a separate apparatus than the microscope used for readout.

These innovations will result in more accurate measurements, and will enable parallel force application to thousands to millions of calipers per solid support simultaneously. Imaging of the nanoparticles can be achieved with a high-speed camera system, which is a powerful and convenient way to track nanoparticles. Various reporter moieties can be incorporated into the NCT such as gold nanoparticles, fluorophores, quantum dots or DNA origami structures, depending on the preferred microscopy system.

Figure 5:
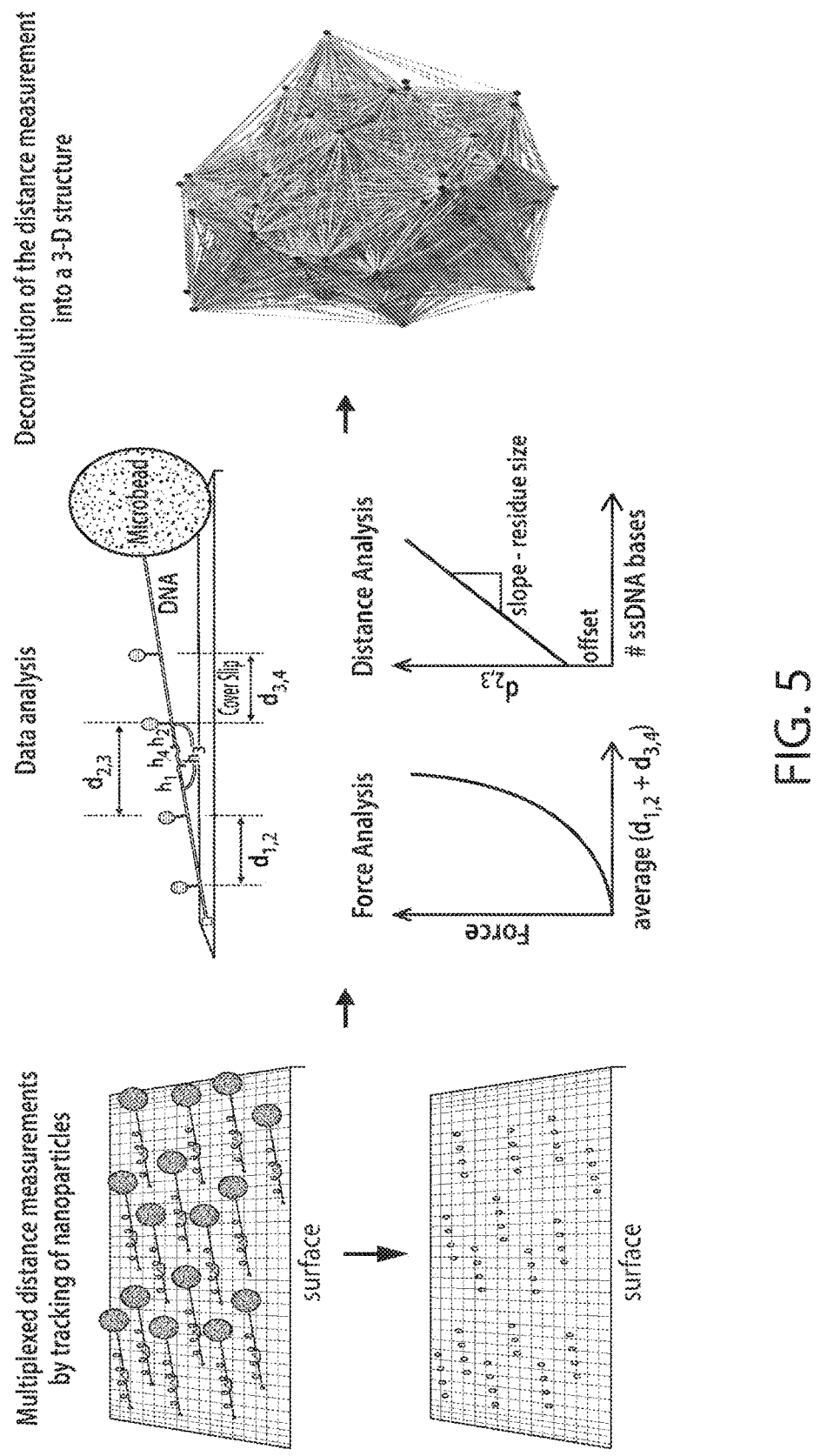
FIG. 5. Overview of high-resolution nanoparticle imaging and subsequent data analysis. Representation of an image obtained by visualizing the tracking nanoparticles. Tracking the nanoparticles will provide simultaneously the force exerted on the NCT in real time and the measured distance of the analyte. The collected distance measurements can then be used for reconstruction of a 3-D structure of the measured analyte.

The distance can be calibrated, and the temporal and spatial resolution assessed by adopting methods from super resolution microscopy to localize and track the reporter moieties such as nanoparticles. Measuring the distance between particle a1, a2 (d1,2) and a3, a4 (d3,4), respectively at different levels of applied force (FIG. 5) and fitting to a worm-like chain model, allows for a calibration curve to be established to enable independent determination of the force exerted on each NCT. Averaging the distances d1,2 and d3,4 will increase the accuracy of the force measurements. The pairwise distance between handles on a target analyte are determined by measuring the distance between nanoparticles a2 and a3 on either side of the target analyte (d2,3) (FIG. 5).

Targets

A variety of targets can be analyzed using the methods of this disclosure. The only limitation on the target is that it must be amenable to being bound to a nucleic acid directly or indirectly. The target may be without limitation a protein, a polypeptide, a peptide, a nucleic acid, a virus-like particle, a steroid, a proteoglycan, a lipid, a carbohydrate, and analogs, derivatives, mixtures, fusions, combinations or conjugates thereof.

One class of targets is peptide-based targets such as (single or multi-chain) proteins and peptides. Examples of peptide-based targets include without limitation antibodies, single chain antibodies, antibody fragments, enzymes, co-factors, receptors, ligands, transcription factors and other regulatory factors, some antigens (as discussed below), cytokines, chemokines, hormones, and the like.

In some embodiments, inorganic or synthetic agents can be analyzed. Such inorganic or synthetic agents include inorganic non-particles and synthetic polymers.

Modification of Targets

The surface of the target (e.g., multiprotein complex) may be decorated covalently with ssDNA handles to create points of attachment to the caliper. Carbodiimide activation followed by reaction with amines can be used for specific modification of aspartate and glutamate residues, although preferably lysines are consumed or protected beforehand to prevent unwanted cross-reaction. Mendoza and Vachet, Probing Protein Structure by Amino Acid-Specific Covalent Labeling and Mass Spectrometry; Mass Spectrom Rev, 28(5):785-815, 2009, report methods for amino acid specific modification of eight kinds of residues as follows:

A. arginine (e.g. reaction with phenylglyoxal)

B. carboxylate (aspartate and glutamate) (e.g. activation by carbodiimide then reaction with amino-oxy)

C. cysteine (e.g. reaction with maleimide)

D. histidine (e.g. reaction with diethylpyrocarbonate)

E. lysine (e.g. reaction with NHS ester)

F. tryptophan (e.g. reaction with 2-hydroxy-5-nitrobenzyl bromide)

G. tyrosine (e.g. reaction with tetranitromethane, iodine, or N-acetylimidazole)

If analysis of targets only in the denatured state is desired, then decoration with ssDNA handles can be done under denaturing conditions, e.g., in the presence of 6 M GuCl, 8 M urea, or 1% SDS. Therefore positions buried on the inside of the native structure can be accessible for labeling.

Applications and Uses

The methods provided herein can be used to determine (or map) the surface structure of proteins of known primary amino acid sequence. In these instances, the attachment points to a target protein will be known (due to the known reactivity and specificity of the reagents used for attachment). For example, it will be known that the attachment points are lysines because an NHS reactive group will be used to attach. Initially, the distance between the lysines is determined when the target protein is in its native conformation. This distance is used to map the surface structure of the target protein. It will not be known which specific lysines are involved, since the attachment to the target protein is random and could be to any surface lysines available for reaction. However, the target protein is then stretched under denaturing conditions (such as but not limited to in the presence of SDS), allowing the distance between the two lysines to be determined when the target protein is denatured. This latter distance will then be used to identify which lysines are involved by comparison to the known primary amino acid sequence.

The methods can also be used to determine (or map) the surface structure of a protein of unknown primary amino acid sequence. A similar approach to that described above can be used except that more iterations of the process are likely necessary. In the process, the primary amino acid sequence will also be partially determined.

The ability to identify a target allows its presence to be determined in a sample or as a result of an event. Accordingly, the methods can be used as detection or diagnostic methods to determine the presence (or absence) of a target. This may have a wide range of uses, including clinical uses.

The methods can also be used to determine changes in structure to a target as a result of binding to a known or unknown binding partner or to determine changes in structure in response to applied force(s). Typically, the target structure when in an unbound state is known or determined. Examples of binding partners include putative drug candidates such as allosteric inhibitors or activators (e.g., activators of enzymes such as kinases). In this way, the methods can be used in massively parallel drug screening assays. The methods can also be used for single-particle detection or proteomics, for example identification of viruses. They can further be used for rapid structural characterization of synthetic-biology devices, such as artificial protein machines.

Nucleic Acids

The nucleic acid structures may comprise naturally occurring and/or non-naturally occurring nucleic acids. If naturally occurring, the nucleic acids may be isolated from natural sources or they may be synthesized apart from their naturally occurring sources. Non-naturally occurring nucleic acids are synthetic.

The terms "nucleic acid", "oligonucleotide", and "strand" are used interchangeably to mean multiple nucleotides attached to each other in a contiguous manner. A nucleotide is a molecule comprising a sugar (e.g. a deoxyribose) linked to a phosphate group and to an exchangeable organic base, which is either a pyrimidine (e.g., cytosine (C), thymidine (T) or uracil (U)) or a purine (e.g., adenine (A) or guanine (G)). In some embodiments, the nucleic acid may be L-DNA. In some embodiments, the nucleic acid is not RNA or an oligoribonucleotide. In these embodiments, the nucleic acid structure may be referred to as a DNA structure. A DNA structure however may still comprise base, sugar and backbone modifications.

Modifications

A nucleic acid structure may be made of DNA, modified DNA, and combinations thereof. The oligodeoxyribonucleotides (which are included in the class of oligonucleotides as used herein) that are used to generate the nucleic acid structure or that are present in the nucleic acid structure may have a homogeneous or heterogeneous (i.e., chimeric) backbone. The backbone may be a naturally occurring backbone such as a phosphodiester backbone or it may comprise backbone modification(s). In some instances, backbone modification results in a longer half-life for the oligonucleotides due to reduced nuclease-mediated degradation. This in turn results in a longer half-life. Examples of suitable backbone modifications include but are not limited to phosphorothioate modifications, phosphorodithioate modifications, p-ethoxy modifications, methylphosphonate modifications, methylphosphorothioate modifications, alkyl- and arylphosphates (in which the charged phosphonate oxygen is replaced by an alkyl or aryl group), alkylphosphotriesters (in which the charged oxygen moiety is alkylated), peptide nucleic acid (PNA) backbone modifications, locked nucleic acid (LNA) backbone modifications, and the like. These modifications may be used in combination with each other and/or in combination with phosphodiester backbone linkages.

Alternatively or additionally, the oligonucleotides may comprise other modifications, including modifications at the base or the sugar moieties. Examples include nucleic acids having sugars which are covalently attached to low molecular weight organic groups other than a hydroxyl group at the 3' position and other than a phosphate group at the 5' position (e.g., a 2'-O-alkylated ribose), nucleic acids having sugars such as arabinose instead of ribose. Nucleic acids also embrace substituted purines and pyrimidines such as C-5 propyne modified bases (Wagner et al., Nature Biotechnology 14:840-844, 1996). Other purines and pyrimidines include but are not limited to 5-methylcytosine, 2-aminopurine, 2-amino-6-chloropurine, 2,6-diaminopurine, hypoxanthine. Other such modifications are well known to those of skill in the art.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863, and alkylphosphotriesters (in which the charged oxygen moiety is alkylated as described in U.S. Pat. No. 5,023,243 and European Patent No. 092574) can be prepared by automated solid phase synthesis using commercially available reagents. Methods for making other DNA backbone modifications and substitutions have been described (Uhlmann, E. and Peyman, A., Chem. Rev. 90: 5 544, 1990; Goodchild, J., Bioconjugate Chem. 1:165, 1990).

Nucleic acids can be synthesized de novo using any of a number of procedures known in the art including, for example, the b-cyanoethyl phosphoramidite method (Beaucage and Caruthers Tet. Let. 22:1859, 1981), and the nucleoside H-phosphonate method (Garegg et al., Tet. Let. 27:4051-4054, 1986; Froehler et al., Nucl. Acid. Res. 14:5399-5407, 1986; Garegg et al., Tet. Let. 27:4055-4058, 1986, Gaffney et al., Tet. Let. 29:2619-2622, 1988). These chemistries can be performed by a variety of automated nucleic acid synthesizers available in the market. These nucleic acids are referred to as synthetic nucleic acids. Modified and unmodified nucleic acids may also be purchased from commercial sources such as IDT, Twist Biosciences, and Bioneer.

Isolation, as used herein, refers to the physical separation of the desired entity (e.g., nucleic acid structures, etc.) from the environment in which it normally or naturally exists or the environment in which it was generated. The isolation may be partial or complete. An isolated nucleic acid generally refers to a nucleic acid that is separated from components with which it normally associates in nature. As an example, an isolated nucleic acid may be one that is separated from a cell, from a nucleus, from mitochondria, or from chromatin.

The nucleic acid nanostructures may be isolated and/or purified. Isolation of the nucleic acid nanostructure may be carried out by running a hybridization reaction mixture on a gel and isolating nucleic acid structures that migrate at a particular molecular weight and are thereby distinguished from the nucleic acid substrates and the spurious products of the hybridization reaction. As another example, isolation of nucleic acid structures may be carried out using a buoyant density gradient, sedimentation gradient centrifugation, or through filtration means.

---

What is claimed is:

1. A method of performing distance measurements of a protein, comprising providing a nucleic acid-protein complex comprising a nucleic acid having a plurality of single-stranded branched oligonucleotides (T1-T6), covalently attached using non-phosphodiester bonds, at predetermined distances along its length, a first subset of branched oligonucleotides having reporter moieties at their free ends (T1, T2, T5, T6), and a protein having first and second single-stranded nucleic acid handles (SS nucleic acid handles) attached to first and second adjacent, internal branched oligonucleotides (T3, T4), wherein a first end of the nucleic acid is attached to a solid support and a second end of the nucleic acid is attached to a bead, applying a force on the complex in the direction of the bead, and performing one or both of (i) and (ii) wherein (i) comprises detecting location of one or more of the branched oligonucleotides having reporter moieties at their free ends under force and in the absence of force, wherein a change in location under force relative to in the absence of force represents a distance between the first and second SS nucleic acid handles, and (ii) comprises measuring distance between a pair of reporter moieties under force and in the absence of force, wherein a change in distance between a pair of reporter moieties under force relative to in the absence of force represents a distance between the first and second SS nucleic acid handles, wherein the pair of reporter moieties is selected from T1 and T6, T1 and T5, T2 and T5, and T2 and T6.

2. A method of performing distance measurements of a protein, comprising providing a nucleic acid-protein complex comprising (1) a nucleic acid covalently attached using non-phosphodiester bonds, at pre-determined distances along its length, to six single-stranded branched oligonucleotides (T1-T6), the first, second, fifth and sixth branched oligonucleotides (T1, T2, T5, T6) having reporter moieties at their free ends, and (2) a protein having first and second single-stranded nucleic acid handles (SS nucleic acid handles) attached to the third and fourth branched oligonucleotides (T3, T4), wherein a first end of the nucleic acid is attached to a solid support and a second end of the nucleic acid is attached to a bead, applying a force on the complex in the direction of the bead, and performing one or both of (i) and (ii) wherein (i) comprises detecting the location of one or more of the reporter moieties attached to T1, T2, T5 and T6 under force and in the absence of force, wherein a change in location under force relative to in the absence of force represents a distance between the first and second SS nucleic acid handles on the protein, and (ii) comprises measuring distance between reporter moieties attached to T1 and T6 or T1 and T5 or T2 and T5 or T2 and T6 under force and in the absence of force, wherein a change in distance under force relative to in the absence of force represents a distance between the first and second SS nucleic acid handles on the protein.

3. The method of claim 2, further comprising detaching the fourth branched oligonucleotide (T4) from the second SS nucleic acid handle, attaching the fourth branched oligonucleotide to a third SS nucleic acid handle on the protein, re-applying a force on the complex in the direction of the bead, and performing one or both of (i) and (ii), wherein (i) comprises detecting the location of one or more of the reporter moieties attached to T1, T2, T5 and T6 under force and in the absence of force, wherein a change in location under force relative to in the absence of force represents a distance between the first and third SS nucleic acid handles on the protein, and (ii) comprises measuring distance between reporter moieties attached to T1 and T6 or T1 and T5 or T2 and T5 or T2 and T6 under force and in the absence of force, wherein a change in distance under force relative to in the absence of force represents a distance between the first and third SS nucleic acid handles on the protein.

4. The method of claim 1, further comprising detaching the fourth branched oligonucleotide (T4) from the second SS nucleic acid handle, attaching the fourth branched oligonucleotide to a third SS nucleic acid handle on the protein, re-applying a force on the complex in the direction of the bead, and performing one or both of (i) and (ii), wherein (i) comprises detecting the location of one or more of the branched oligonucleotides having reporter moieties attached at their free ends under force and in the absence of force, wherein a change in location under force relative to in the absence of force represents a distance between the first and third SS nucleic acid handles on the protein, and (ii) comprises measuring distance between a pair of reporter moieties under force and in the absence of force, wherein a change in distance between a pair of reporter moieties under force relative to in the absence of force represents a distance between the first and third SS nucleic acid handles on the protein, wherein the pair of reporter moieties is selected from T1 and T6, T1 and T5, T2 and T5, and T2 and T6.

5. The method of claim 1, further comprising measuring a change in distance between T1 and T2 or between T5 and T6, under force and in the absence of force.

6. The method of claim 1, wherein the nucleic acid is a DNA and the branched oligonucleotides are DNA.

7. The method of claim 1, wherein the nucleic acid is 5 kb to 20 kb in length and the each of the branched oligonucleotides is 10-50 nucleotides in length.

8. The method of claim 1, wherein the first subset of branched oligonucleotides has identical nucleotide sequences.

9. The method of claim 1, wherein the reporter moieties are identical.

10. The method of claim 1, wherein the first and second SS nucleic acid handles are both attached to cysteines or to lysines.

11. The method of claim 1, wherein the force is centrifugal force, gravitational force, magnetic force, or laterally directed flow.

12. The method of claim 1, wherein in (ii), the distance measured is between T1 and T6 or T2 and T5, under force and in the absence of force.

13. The method of claim 2, further comprising measuring a change in distance between T1 and T2 or between T5 and T6, under force and in the absence of force.

14. The method of claim 2, wherein the nucleic acid is a DNA and the branched oligonucleotides are DNA.

15. The method of claim 2, wherein the nucleic acid is 5 kb to 20 kb in length and the each of the branched oligonucleotides is 10-50 nucleotides in length.

16. The method of claim 2, wherein the branched oligonucleotides having reporter moieties at their free ends have identical nucleotide sequences.

17. The method of claim 2, wherein the reporter moieties are identical.

18. The method of claim 2, wherein the first and second SS nucleic acid handles are both attached to cysteines or to lysines.

19. The method of claim 2, wherein the force is centrifugal force, gravitational force, magnetic force, or laterally directed flow.

20. The method of claim 2, wherein in (ii), the distance measured is between T1 and T6 or T2 and T5, under force and in the absence of force.

* * * * *

```
                           SEQUENCE LISTING

<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: Synthetic

<400> SEQUENCE: 1
caccagagac ctcgaggtct caccag                                            26

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
ctggtgagac ctcgaggtct ctggtg                                            26

<210> SEQ ID NO 3
<211> LENGTH: 16
<212> TYPE: DNA
<213> ORGANISM: Artificial Sequence
<220> FEATURE:
<223> OTHER INFORMATION: Synthetic

<400> SEQUENCE: 3
ctcgaggtct cacacc                                                       16

<210> SEQ ID NO 4
<211> LENGTH: 16
<212> TYPE: DNA
<213> ORGANISM: Artificial Sequence
<220> FEATURE:
<223> OTHER INFORMATION: Synthetic

<400> SEQUENCE: 4
ggtgtgagac ctcgag                                                       16

<210> SEQ ID NO 5
<211> LENGTH: 16
```

-continued

```
<212> TYPE: DNA
<213> ORGANISM: Artificial Sequence
<220> FEATURE:
<223> OTHER INFORMATION: Synthetic

<400> SEQUENCE: 5
cctgagagac ctcgag                                                              16

<210> SEQ ID NO 6
<211> LENGTH: 16
<212> TYPE: DNA
<213> ORGANISM: Artificial Sequence
<220> FEATURE:
<223> OTHER INFORMATION: Synthetic

<400> SEQUENCE: 6
ctcgaggtct ctcagg                                                              16

<210> SEQ ID NO 7
<211> LENGTH: 26
<212> TYPE: DNA
<213> ORGANISM: Artificial Sequence
<220> FEATURE:
<223> OTHER INFORMATION: Synthetic

<400> SEQUENCE: 7
gtcgagagac ctcgaggtct cacctg                                                   26

<210> SEQ ID NO 8
<211> LENGTH: 26
<212> TYPE: DNA
<213> ORGANISM: Artificial Sequence
<220> FEATURE:
<223> OTHER INFORMATION: Synthetic

<400> SEQUENCE: 8
caggtgagac ctcgaggtct ctcgac                                                   26

<210> SEQ ID NO 9
<211> LENGTH: 23
<212> TYPE: PRT
<213> ORGANISM: Artificial Sequence
<220> FEATURE:
<223> OTHER INFORMATION: Synthetic

<400> SEQUENCE: 9

Ala Arg Thr Gly Gly Gly Gly Ser Gly Gly Gly Ser Gly Gly Gly Gly
1               5                   10                  15

Ser Gly Gly Gly Gly Ser Cys
            20
```